United States Patent
Auge, II et al.

(10) Patent No.: US 10,016,230 B2
(45) Date of Patent: **\*Jul. 10, 2018**

(54) SYSTEM AND METHOD FOR A PHYSIOCHEMICAL SCALPEL TO ELIMINATE BIOLOGIC TISSUE OVER-RESECTION AND INDUCE TISSUE HEALING

(71) Applicant: NuOrtho Surgical, Inc., Fall River, MA (US)

(72) Inventors: Wayne K. Auge, II, Santa Fe, NM (US); Roy E. Morgan, Alameda, CA (US)

(73) Assignee: NUORTHO SURGICAL, INC., Fall River, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/232,473

(22) Filed: Aug. 9, 2016

(65) Prior Publication Data

US 2017/0035490 A1 Feb. 9, 2017

Related U.S. Application Data

(63) Continuation of application No. 13/405,044, filed on Feb. 24, 2012, now Pat. No. 9,408,658.

(Continued)

(51) Int. Cl.
*A61B 18/04* (2006.01)
*A61B 18/14* (2006.01)
(Continued)

(52) U.S. Cl.
CPC .............. *A61B 18/14* (2013.01); *A61B 18/12* (2013.01); *A61N 1/325* (2013.01); *A61N 1/326* (2013.01);
(Continued)

(58) Field of Classification Search
CPC . A61B 18/12; A61B 2018/1472; A61B 18/14; A61N 1/44; A61N 1/325; A61N 1/326; A61N 1/327; A61N 1/40
See application file for complete search history.

(56) References Cited

U.S. PATENT DOCUMENTS

| | | | |
|---|---|---|---|
| 3,903,891 A | 9/1975 | Brayshaw | |
| 3,911,107 A | 10/1975 | Krezanoski | |

(Continued)

FOREIGN PATENT DOCUMENTS

| | | |
|---|---|---|
| GB | 2037920 | 7/1980 |
| WO | 1996/00042 | 1/1996 |

(Continued)

OTHER PUBLICATIONS

Auge, "Redox Magnetohydrodynamic Engineered Irrigants Are Based Upon Constituent Charege-to-mass Ratio Profiles", 6th Annual Conference on the Physics, Chemistry, and Biology of Water, Oct. 20, 2011.

(Continued)

*Primary Examiner* — Lindsey G Wehrheim
(74) *Attorney, Agent, or Firm* — Peacock Law P.C.; Janeen Vilven; Deborah Peacock

(57) ABSTRACT

Removal of damaged tissue itself can enable biosynthetic activity in vivo as an unburdened homeostatic or repair response. By removing a biologic and mechanical irritant, the lesion site can be altered to a more favorable perturbation-specific mechanotransductive environment supportive of differentiated gene expression. One aspect of one embodiment of the present invention provides an engineered irrigant that produces ion exchanges in tissues for example deliver of protons which interact with biology tissues.

19 Claims, 13 Drawing Sheets
(4 of 13 Drawing Sheet(s) Filed in Color)

Related U.S. Application Data

(60) Provisional application No. 61/446,463, filed on Feb. 24, 2011, provisional application No. 61/547,566, filed on Oct. 14, 2011.

(51) Int. Cl.
  *A61B 18/12* (2006.01)
  *A61N 1/32* (2006.01)
  *A61N 1/40* (2006.01)
  *A61N 1/44* (2006.01)

(52) U.S. Cl.
  CPC .............. *A61N 1/327* (2013.01); *A61N 1/40* (2013.01); *A61N 1/44* (2013.01); *A61B 2018/1472* (2013.01)

(56) References Cited

U.S. PATENT DOCUMENTS

| | | | |
|---|---|---|---|
| 3,941,135 A | 3/1976 | Von Sturm et al. |
| 3,982,017 A | 9/1976 | Thiele |
| 4,014,777 A | 3/1977 | Brown |
| 4,060,088 A | 11/1977 | Morrison et al. |
| 4,094,320 A | 6/1978 | Newton |
| 4,105,017 A | 8/1978 | Ryaby et al. |
| 4,231,372 A | 11/1980 | Newton |
| 4,237,887 A | 12/1980 | Gonser |
| 4,266,532 A | 5/1981 | Ryaby et al. |
| 4,266,533 A | 5/1981 | Ryaby et al. |
| 4,343,308 A | 8/1982 | Gross |
| 4,416,277 A | 11/1983 | Newton et al. |
| 4,504,493 A | 3/1985 | Marshall et al. |
| 4,540,409 A | 9/1985 | Nystrom et al. |
| 4,559,036 A | 12/1985 | Wunsch |
| 4,615,347 A | 10/1986 | Schooley |
| 4,827,927 A | 5/1989 | Newton |
| D301,739 S | 6/1989 | Turner et al. |
| 4,872,865 A | 10/1989 | Bloebaum et al. |
| 4,901,719 A | 2/1990 | Trenconsky et al. |
| 4,938,970 A | 7/1990 | Hustead et al. |
| 4,971,068 A | 11/1990 | Sahi |
| 5,014,699 A | 5/1991 | Pollack et al. |
| 5,236,456 A | 8/1993 | O'Leary et al. |
| 5,282,861 A | 2/1994 | Kaplan |
| 5,304,724 A | 4/1994 | Newton |
| 5,314,476 A | 5/1994 | Prewett et al. |
| 5,342,357 A | 8/1994 | Nardella |
| 5,352,463 A | 10/1994 | Badylak et al. |
| 5,360,440 A | 11/1994 | Andersen |
| 5,364,395 A | 11/1994 | West, Jr. et al. |
| 5,366,443 A | 11/1994 | Eggers et al. |
| 5,403,825 A | 4/1995 | Lagarde et al. |
| 5,458,596 A | 10/1995 | Lax et al. |
| 5,472,442 A | 12/1995 | Klicek |
| 5,494,538 A | 2/1996 | Kirillov et al. |
| 5,498,259 A | 3/1996 | Mourant et al. |
| 5,514,130 A | 5/1996 | Baker |
| 5,516,533 A | 5/1996 | Badylak et al. |
| 5,554,141 A | 9/1996 | Wendler |
| 5,569,241 A | 10/1996 | Edwards |
| 5,569,242 A | 10/1996 | Lax et al. |
| 5,573,424 A | 11/1996 | Poppe |
| 5,584,863 A | 12/1996 | Rauch et al. |
| 5,622,725 A | 4/1997 | Kross |
| 5,633,578 A | 5/1997 | Eggers et al. |
| 5,669,904 A | 9/1997 | Platt et al. |
| 5,669,907 A | 9/1997 | Platt et al. |
| 5,669,934 A | 9/1997 | Sawyer |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,741,261 A | 4/1998 | Moskovitz et al. |
| 5,746,896 A | 5/1998 | Shimamune et al. |
| 5,749,895 A | 5/1998 | Sawyer et al. |
| 5,772,659 A | 6/1998 | Becker et al. |
| 5,788,976 A | 8/1998 | Bradford |
| 5,797,902 A | 8/1998 | Netherly |
| 5,800,385 A | 9/1998 | Demopuls et al. |
| 5,820,583 A | 10/1998 | Demopolos et al. |
| 5,824,015 A | 10/1998 | Sawyer |
| 5,840,166 A | 11/1998 | Kaneko |
| 5,855,608 A | 1/1999 | Brekke |
| 5,860,950 A | 1/1999 | Demopulos et al. |
| 5,871,469 A | 2/1999 | Eggers et al. |
| 5,885,277 A | 3/1999 | Korth |
| 5,885,292 A | 3/1999 | Moskovitz et al. |
| 5,891,140 A | 4/1999 | Ginn et al. |
| 5,919,191 A | 6/1999 | Lennox et al. |
| 5,955,514 A | 9/1999 | Huang et al. |
| 5,964,968 A | 10/1999 | Kaneko |
| 6,007,532 A | 12/1999 | Netherly |
| 6,032,077 A | 2/2000 | Pomeranz |
| 6,033,654 A | 3/2000 | Stedronsky et al. |
| 6,056,746 A | 5/2000 | Goble et al. |
| 6,068,627 A | 5/2000 | Orszulak et al. |
| 6,086,585 A | 7/2000 | Hovda et al. |
| 6,093,186 A | 7/2000 | Goble |
| 6,112,122 A | 8/2000 | Schwardt et al. |
| 6,113,596 A | 9/2000 | Hooven et al. |
| 6,117,109 A | 9/2000 | Eggers et al. |
| 6,135,998 A | 10/2000 | Palanker |
| D433,752 S | 11/2000 | Saravia |
| 6,142,992 A | 11/2000 | Cheng et al. |
| 6,149,620 A | 11/2000 | Baker et al. |
| 6,159,194 A | 12/2000 | Eggers et al. |
| 6,162,219 A | 12/2000 | Nilsson et al. |
| 6,174,309 B1 | 1/2001 | Wrublewski et al. |
| 6,203,541 B1 | 3/2001 | Keppel |
| 6,206,875 B1 | 3/2001 | Long et al. |
| 6,206,878 B1 | 3/2001 | Bishop et al. |
| 6,207,134 B1 | 3/2001 | Fahlvik et al. |
| 6,210,403 B1 | 4/2001 | Klicek et al. |
| 6,213,999 B1 | 4/2001 | Platt et al. |
| 6,214,003 B1 | 4/2001 | Morgan et al. |
| 6,224,592 B1 | 5/2001 | Eggers et al. |
| 6,235,024 B1 | 5/2001 | Tu |
| 6,241,723 B1 | 6/2001 | Heim et al. |
| 6,241,753 B1 | 6/2001 | Knowlton |
| 6,258,088 B1 | 7/2001 | Tzonev et al. |
| 6,261,286 B1 | 7/2001 | Goble et al. |
| 6,264,650 B1 | 7/2001 | Hovda et al. |
| 6,264,652 B1 | 7/2001 | Eggers et al. |
| 6,273,883 B1 | 8/2001 | Furumoto |
| 6,293,942 B1 | 9/2001 | Goble et al. |
| 6,296,636 B1 | 10/2001 | Cheng et al. |
| 6,306,134 B1 | 10/2001 | Goble et al. |
| 6,309,387 B1 | 10/2001 | Eggers et al. |
| 6,322,549 B1 | 11/2001 | Eggers et al. |
| 6,325,799 B1 | 12/2001 | Goble |
| 6,350,276 B1 | 1/2002 | Knowlton |
| 6,371,967 B1 | 4/2002 | Long et al. |
| 6,383,184 B1 | 5/2002 | Sharkey |
| 6,391,025 B1 | 5/2002 | Weinstein et al. |
| 6,416,509 B1 | 7/2002 | Goble et al. |
| 6,419,815 B1 | 7/2002 | Chambers et al. |
| 6,442,418 B1 | 8/2002 | Evans et al. |
| 6,461,352 B2 | 10/2002 | Morgan et al. |
| 6,463,336 B1 | 10/2002 | Mawhinney |
| 6,471,993 B1 | 10/2002 | Shastri et al. |
| 6,547,794 B2 | 4/2003 | Auge |
| 6,558,382 B2 | 5/2003 | Jahns et al. |
| 6,743,248 B2 | 6/2004 | Edwards et al. |
| D495,076 S | 8/2004 | Mandel |
| 6,772,013 B1 | 8/2004 | Ingle et al. |
| 6,780,178 B2 | 8/2004 | Palanker et al. |
| 6,824,555 B1 | 11/2004 | Towler et al. |
| 6,832,995 B1 | 12/2004 | Towler et al. |
| D501,047 S | 1/2005 | Breazeale et al. |
| 6,890,332 B2 | 5/2005 | Truckai et al. |
| 6,902,564 B2 | 6/2005 | Morgan et al. |
| 7,004,939 B2 | 2/2006 | MacKay |
| 7,066,932 B1 | 6/2006 | Morgan et al. |

(56) References Cited

U.S. PATENT DOCUMENTS

| | | | |
|---|---|---|---|
| 7,105,011 | B2 | 9/2006 | Auge |
| 7,131,860 | B2 | 11/2006 | Sartor et al. |
| 7,137,980 | B2 | 11/2006 | Buysse et al. |
| D535,396 | S | 1/2007 | Reschke et al. |
| 7,160,293 | B2 | 1/2007 | Sturm et al. |
| 7,300,435 | B2 | 11/2007 | Wham et al. |
| 7,354,438 | B2 | 4/2008 | Morgan et al. |
| 7,367,976 | B2 | 5/2008 | Lawes et al. |
| 7,393,354 | B2 | 7/2008 | Buchman et al. |
| 7,416,437 | B2 | 8/2008 | Sartor et al. |
| 7,438,714 | B2 | 10/2008 | Phan |
| D581,530 | S | 11/2008 | Thierfelder et al. |
| 7,445,619 | B2 | 11/2008 | Auge et al. |
| 7,481,810 | B2 | 1/2009 | Drumbauld et al. |
| D587,803 | S | 3/2009 | Di Sessa et al. |
| D588,696 | S | 3/2009 | Mantle et al. |
| 7,503,917 | B2 | 3/2009 | Sartor et al. |
| 7,549,989 | B2 | 6/2009 | Morgan et al. |
| 7,713,269 | B2 | 5/2010 | Auge et al. |
| 7,771,422 | B2 | 8/2010 | Auge et al. |
| 7,819,861 | B2 | 10/2010 | Auge |
| 7,819,864 | B2 | 10/2010 | Morgan et al. |
| 7,879,034 | B2 | 2/2011 | Woloszko et al. |
| 7,955,296 | B1 | 6/2011 | Morgan et al. |
| 8,235,979 | B2 | 8/2012 | Morgan et al. |
| 8,361,065 | B2 | 1/2013 | West, Jr. |
| 8,591,508 | B2 | 11/2013 | Morgan et al. |
| 8,623,012 | B2 | 1/2014 | Morgan et al. |
| 8,734,441 | B2 | 5/2014 | Morgan et al. |
| 9,408,658 | B2 * | 8/2016 | Auge, II ............... A61N 1/44 |
| 2001/0007940 | A1 | 7/2001 | Tu et al. |
| 2001/0039419 | A1 | 11/2001 | Francischelli et al. |
| 2002/0165596 | A1 | 11/2002 | Wilson |
| 2002/0183737 | A1 | 12/2002 | Kristensen |
| 2003/0004508 | A1 | 1/2003 | Morgan et al. |
| 2003/0028189 | A1 | 2/2003 | Woloszko et al. |
| 2003/0036753 | A1 | 2/2003 | Morgan et al. |
| 2003/0216732 | A1 | 11/2003 | Truckai et al. |
| 2003/0216733 | A1 | 11/2003 | McClurken et al. |
| 2004/0030330 | A1 | 2/2004 | Brassell et al. |
| 2004/0082945 | A1 | 4/2004 | Clague et al. |
| 2004/0082946 | A1 | 4/2004 | Malis et al. |
| 2004/0167244 | A1 | 8/2004 | Auge, II |
| 2004/0267255 | A1 | 12/2004 | Auge, II et al. |
| 2005/0015085 | A1 | 1/2005 | McClurken et al. |
| 2005/0085806 | A1 | 4/2005 | Auge, II et al. |
| 2005/0182449 | A1 | 8/2005 | Auge, II et al. |
| 2005/0283151 | A1 | 12/2005 | Ebbutt et al. |
| 2006/0079873 | A1 | 4/2006 | Scopton et al. |
| 2006/0210552 | A1 | 9/2006 | Demopulos et al. |
| 2007/0016182 | A1 | 1/2007 | Lipson et al. |
| 2008/0065056 | A1 | 3/2008 | Powell et al. |
| 2008/0183164 | A1 | 7/2008 | Elkins et al. |
| 2008/0281316 | A1 | 11/2008 | Carlton et al. |
| 2008/0287948 | A1 | 11/2008 | Newton et al. |
| 2009/0030410 | A1 | 1/2009 | Auge, II et al. |
| 2009/0306645 | A1 | 12/2009 | Morgan et al. |
| 2010/0069975 | A1 | 3/2010 | Auge |
| 2010/0087815 | A1 | 4/2010 | Morgan et al. |
| 2010/0262136 | A1 | 10/2010 | Morgan |
| 2011/0034914 | A1 | 2/2011 | Auge et al. |
| 2011/0087308 | A1 | 4/2011 | Morgan et al. |
| 2011/0196366 | A1 | 8/2011 | Humble |
| 2011/0288547 | A1 | 11/2011 | Morgan et al. |
| 2013/0060249 | A1 | 3/2013 | Maeda et al. |

FOREIGN PATENT DOCUMENTS

| | | |
|---|---|---|
| WO | 2002/102438 | 12/2002 |
| WO | WO03/015865 | 2/2003 |
| WO | 2003/103522 | 6/2003 |
| WO | 2003/103521 | 12/2003 |
| WO | 2011/047148 | 4/2011 |

OTHER PUBLICATIONS

Babincova, et al., "High-Gradient Magnetic Capture of Ferrofluids: Implications for Drug Targeting and Tumor Embolization", Zeitschrift fur Naturforschung vol. 56-C, 2001, 909-911.

Brennetot, et al., "Investigation of Chelate Formation, Intramolecular Energy Transfer and Luminescence Efficiency and Lifetimes in the Eu-thenoyltrifluoroacetone-trioctylphosphine oxide-Triton x-100 System Using Absorbance, Fluorescence and Photothermal Measurements", Spectrochim Acta Part A 56, 2000, 703-715.

Chen, et al., "Heat-Induced Changes in the Mechanics of a Collagenous Tissue: Isothermal, Isotonic Shrinkage", Transactions of the ASME vol. 120, 1998, 382-388.

Edwards, et al., "Thermometric Determination of Cartilage Matrix Temperatures During Thermal Chondroplasty: Comparison of Bipolar and Monopolar Radiofrequency Devices", Arthroscopy vol. 18 No. 4, 2002, 339-346.

Fink, et al., "Holmium: YAG Laser-Induced Aseptic Bone Necroses of the Femoral Condyle", Arthroscopy: The Journal of Arthroscopic and Related Surgery vol. 12 No. 2, 1996, 217-223.

Ganguly, et al., "Nanomedical DNA Conduction: Accessing Genomic Control Mechanisms Associated with Biosynthetic Tissue Assembly", Ninth International Nanomedicine and Drug Delivery Symposium, Oct. 15, 2011, 1-5.

Gould, et al., "Cellular Contribution of Bone Graft to Fusion", Journal of Orthopaedic Research vol. 18, 2000, 920-927.

Grant, et al., "Magentic Field-Controlled Microfluidic Transport", Journal of Americal Chemical Society vol. 124 No. 3, 2002, 462-467.

Ito, et al., "Sensitivity of Osteoinductive Activity of Deminerlization and Defatted Rat Femur to Temperature and Duration of Heating", Clinical Orthopaedics and Related Research No. 316, 1995, 267-275.

Janzen, et al., "Osteonecrosis After Contact Neodymium: Yttrium Aluminum Garnet Arthroscopic Laser Meniscectomy", AJR 169, 1997, 855-858.

Lopez, et al., "Effects of Monopolar Radiofrequency Energy on Ovine Joint Capsular Mechanical Properties", Clinical Orthopaedics and Related Research, No. 374, 2000, 286-297.

Medvecky, et al., "Thermal Capsular Shrinkage: Basic Science and Clinical Applications", Arthroscopy vol. 17 No. 6, 2001, 624-635.

Millenbaugh, et al., "Gene Expression Changes in the Skin of Rats Induced by Prolonged 35 GHz Millimeter-Wave Exposure", Radiation Research vol. 169 No. 3, 2010, 288-300.

Minczykowski, et al., "Effects of Magnetic Resonance Imaging on Polymorphonuclear Neutrophil Adhesion", Diagnostics and Medical Technology, Medical Science Monitor vol. 7 No. 3, 2001, 482-488.

Mourant, et al., "Improvements in Laser "Welding" of Chicken Bone Tibias in vitro", Proc. SPIE 2395, Lasers in Surgery: Advanced Characterization, Therapeutics, and Systems V, 478; doi:10.1117/12.209134, 1995, 1-8.

Mourant, et al., "Laser Welding of Bone: Successful in vitro Experiments", Proc. SPIE 2128, Laser Surgery: Advanced Characterization, Therapeutics, and Systems IV, 484, doi:10.1117/12.184934, 1994, 1-5.

Rozbruch, et al., "Osteonecrosis of the Knee Following Arthroscopic Laser Meniscectomy", Arthroscopy: The Journal of Arthroscopic and Related Surgery vol. 12 No. 2, 1996, 245-250.

Thal, et al., "Delayed Articular Cartilage Slough: Two Cases Resulting From Holmium: YAG Laser Damage to Normal Articular Cartilage and a Review of the Literature", Arthroscopy: The Journal of Arthroscopic and Related Surgery vol. 12 No. 1, 1996, 92-94.

Torchilin, et al., "Drug Targeting", European Journal of Pharmaceutical Sciences 11 Suppl 2, 2000, S81-S91.

Wall, et al., "Thermal Modification of Collagen", J. Shoulder Elbow Surg. vol. 8 No. 4, 1999, 339-344.

Wallace, et al., "Electrothermal Shrinkage Reduces Laxity but Alters Creep Behavior in a Lapine Ligament Model", J. Shoulder Elbow Surg. vol. 10 No. 1, 2001, 1-6.

(56) References Cited

OTHER PUBLICATIONS

Weston, et al., "Redox-Magnetohydrodynamic Microfluids Without Cannels and Compatible with Electrochemical Detection Under Immunoassay Conditions", Analytical Chemistry vol. 87 No. 17, 2010, 7068-7072.

Zhang et al., "Effect(s) of the Demineralization Process on the Osteoinductivity of Demineralization Bone Matrix", J. Periodontol vol. 68, No. 11, 1997, 1085-1092.

Zohar, et al., "Thermal Imaging of Receptor-Activated Heat Production in Single Cells", Biophysical Journal vol. 74, 1998, 82-89.

\* cited by examiner

FIG. E

SYSTEM AND METHOD FOR A PHYSIOCHEMICAL SCALPEL TO ELIMINATE BIOLOGIC TISSUE OVER-RESECTION AND INDUCE TISSUE HEALING

CROSS-REFERENCE TO RELATED APPLICATIONS

This application is a continuation of U.S. patent application Ser. No. 13/405,044, entitled "SYSTEM AND METHOD FOR A PHYSIOCHEMICAL SCALPEL TO ELIMINATE BIOLOGIC TISSUE OVER-RESECTION AND INDUCE TISSUE HEALING", filed on Feb. 24, 2012, which claims priority to and the benefit of U.S. Provisional Patent Application No. 61/446,463, entitled "PHYSIOCHEMICAL SCALPEL TO ELIMINATE BIOLOGIC TISSUE OVER-RESECTION AND INDUCE TISSUE HEALING", filed on Feb. 24, 2011, and U.S. Provisional Patent Application No. 61/547,566, entitled "INVERSE MASS RATIO BATTERY AN IN SITU ENERGY SOURCE GENERATED FROM MOTIVE PROTON DELIVERY GRADIENTS", filed on Oct. 14, 2011, the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

Diseased tissue resection at the tissue surface requires precision because tissue surfaces display the shared cell-to-matrix feature of structural stratification. Volumetric or functional over-resection corrupts tissue elements, including intrinsic homeostatic and repair mechanisms, concentrated within the superficial layers at and around these lesions. For many conditions, this imprecision significantly provokes disease progression by eliminating contiguous tissue phenotypes and expanding lesion size toward unsalvageability. The ability to resect diseased tissue precisely, unencumbering contiguous healthy tissue function without iatrogenic impairment of its differentiated phenotype, is a beneficial prerequisite to mitigate the disease burden of tissue-surface based medical conditions. Rather than resection techniques based on imperfect visual-tactile cues designed to unencumber contiguous healthy tissue function, selective targeting of diseased tissue traits protects against the iatrogenic collateral damage of over-resection which can further impair contiguous healthy tissue from retaining and displaying differentiated phenotypes. Early intervention becomes more than an effort to stabilize these lesions into a transient palliative remission indifferent to resection margin accuracy; it becomes a tissue rescue harnessing features unique to tissue surfaces.

Tissue surfaces display a superficial-level healing phenotype because this region is required to interact most intimately with repetitive external tissue-specific stressors. Without these attributes, tissue integrity would be rapidly lost to environmental perturbation. Diseased tissue surfaces manifest as forces or processes overload the tissue's capacity to maintain integrity. Untreated, this tissue burden can ultimately lead to symptoms of disease progression. While the topographic loss of water-structured surface barrier regimes such as stratified zones of structured fluid organized in a potentiometric manner of charge separated areas and the collagen failure of backup layered cleavage planes occur during physiologic loading, these lesions are generally self-repaired by intrinsic tissue assembly mechanisms. The factors by which in vivo self-repair becomes insufficient are complex and tissue-specific. Lesions that remain reversible require targeted resection of the diseased tissue that serves as a biophysical irritant impeding regional tissue organization and assembly. This irritant changes the tissue-surface microenvironment, impeding reconstitution of damaged surface barrier regimes and altering chemo-mechano-transductive gene expression in contiguous tissue, progressively advancing reversible lesions toward failed differentiated homeostatic resistance capacity and an unsalvageable state characterized by non-reversible phenotypic alterations.

Early surgical intervention may be viewed as a tissue rescue, allowing articular cartilage to continue displaying biologic responses appropriate to its function, rather than converting to a tissue ultimately governed by the degenerative material property responses of matrix failure. Early intervention may positively impact the late changes and reduce disease burden of damaged articular cartilage.

A goal of early surgical intervention for treatment of articular cartilage damage is to stabilize lesions as a means to decrease symptoms and disease progression. Lesion stabilization remains a necessary prerequisite toward articular cartilage tissue preservation since removing the irritant of damaged tissue and creating a residually healthy lesion site remain required substrates for permitting or inducing effective in situ healing responses.

For articular cartilage lesion stabilization, thermal and plasma radiofrequency ablation devices originally appeared to be more efficacious than mechanical shavers by exhibiting a smaller time-zero collateral injury footprint. However, because matrix corruption and chondrocyte depletion within contiguous healthy tissue occur commensurate with, and often significantly expand following, volumetric tissue removal, this technology did not become widely adopted as it is understandable that such damage can impair or inhibit in situ healing responses as well as contribute to disease progression by enlarging lesion size. Despite optimizing ablation device performance, this collateral tissue damage transgresses tissue zonal boundaries wherein the depth of necrosis in non-targeted tissue remains larger than native Superficial Zone thickness. Consequently, the functional properties and vital healing phenotype of the Superficial Zone is always effectively eliminated. These collateral wounds originate because ablation technology, like mechanical shavers, cannot distinguish between damaged and undamaged tissue.

Utilizing direct electrode-to-tissue interfaces known in the art indiscriminately deposits current into tissue which causes surface entry wounds and subsurface necrosis through resistive tissue heating and tissue electrolysis; and, because of its high water content, articular cartilage is inherently at risk for efficiently pooling electrothermal energy to a detrimental level. Some have advocated manually positioning the active electrode away from healthy tissue to target diseased tissue. However, this technique significantly increases the amount of current required to overcome the effects that the fluid-flow and convective forces present during surgical application exert on exposed device electrodes. Others have offered that intentional current-based damage serves as a barrier to additional current deposition without demonstrating damage efficacy. Still others utilize current to create ionizing electromagnetic radiation associated with high temperature plasma formation, which has raised further concerns regarding iatrogenic chondrocyte DNA fragmentation and nuclear condensation. Both can induce apoptosis, cellular senescence, decreased progenitor cell populations, diminished cellular differentiation potential, and altered extracellular matrix structure and production. Additional effects of ionizing electromagnetic radiation on chondrocyte behavior important for in situ healing responses remain a cause for concern.

The disturbance of surface-confined nanoscale assemblies in biologic tissue brought about by nonnative interfacial environments during therapeutic intervention has received very little attention despite the significant role these assemblies play in maintaining tissue integrity against perturbation and pathologic solutes. While much has been written about the interfacial nuances of tissue surfaces for over 125 years, the emergence of tissue rescue surgical procedures has generated a renewed interest in surface-confined assemblies because these assemblies are enrolled to produce a healthy lesion site devoid of damaged tissue as a means to unencumber innate and facilitative wound healing. Although becoming increasingly more delineated in various tissue types, surface-confined assemblies remain complex and difficult to study, even without imposing iatrogenic disturbances and non-equilibria treatment conditions. Treatment venues that utilize endoscopic surgical access procedures to care for normally juxtaposed tissue surfaces necessarily involve ambient media replacement and mechanical loading alterations, both of which disturb surface-confined assembly behavior despite attempts to simulate in vivo conditions.

Endoscopic replacement media such as saline solutions were originally intended to aid surgical visualization as native media do not display either consistent or suitable optical properties. Commensurate with this effort were attempts to limit detrimental effects upon interstitial matrices and resident cells, followed by the consideration of medical device performance within replacement media, both without significant deference to surface-confined assembly effects or their reversibility (damaged tissue removal was an obvious entry-level procedural advance once endoscopic access and visualization was made possible. For articular cartilage, early efforts like powered mechanical shavers and electrosurgical (thermal or plasma) ablation devices were based on imperfect visual-tactile cues rather than upon tissue traits that relate the practitioner's ability to distinguish diseased tissue from normal as correlated to conditions that contribute to disease burden. Tissue rescue treatments are designed to unencumber contiguous healthy tissue function by selectively targeting diseased tissue traits to protect against the iatrogenic collateral).

Media replacement eliminates native fluid lubricants required to accommodate physiologic movement between normally juxtaposed tissue surfaces; consequently, interfacial behaviors associated with hydrodynamic fluid film dissolution-depletion occur so that surface asperities are no longer contained within the thickness of native fluid lubricant pools. Such native fluid film starvation is induced by the lower media viscosity associated with optical improvement and the mechanical unloading that occurs by eliminating the normal contact between tissue surfaces. Because pressure build up in native viscous lubricants is inhibited during endoscopy, interruption of other interfacial regimes like squeeze film, interstitial biphasic, mixed-mode, or versions of elastohydrodynamic fluid film mechanisms can inevitably occur (replacement media pressurization within a constrained endoscopic cavity can produce significant hydrostatic forces; and in certain settings, residual lubricant entrapment may occur. Further, the role of hydrodynamic fluid film regimes during endoscopy for porous tissue surfaces like articular cartilage remains to be fully clarified, including the effects porosity may exert upon wettability). These conditions favor the expression of boundary lubrication regimes whereat loading is carried by the surface asperities in a contact area rather than by a fluid film lubricant and at which surface chemistry dominates working properties.

Because the differential mechanical load that tissue surfaces experience during endoscopy is primarily due to surgical device contact, this situation is ideally suited for the treatment of abnormal surface asperities as relative to boundary conditions. Conversely, the disturbances provoked by fluid film starvation and absent hydrodynamic pressure regimes during endoscopy that express boundary conditions constitutes a tissue vulnerability that has been largely unrecognized as an etiologic factor associated with iatrogenic damage that further impairs wound healing, expands lesion size, and contributes to disease burden.

Partial-thickness damaged tissue surfaces at locations requiring relative motion characteristically exhibit abnormal surface asperities and the related absence of surface-confined assemblies associated with boundary lubrication regimes, features that serve as an effective nanoscale trait-targeting substrate for tissue rescue procedures which mimic biologic wound healing behaviors.

Note that the following discussion refers to a number of publications by author(s) and year of publication, and that due to recent publication dates certain publications are not to be considered as prior art vis-a-vis embodiments of the present invention. Discussion of such publications herein is given for more complete background and is not to be construed as an admission that such publications are prior art for patentability determination purposes.

BRIEF SUMMARY OF THE INVENTION

One embodiment of the present invention is a method for treating targeted tissue comprising localizing an alternating current circuit device tip in a saline solution containing electroactive species in which targeted tissue of a host is found and deploying current to the alternating current circuit device tip located in close proximity to the targeted tissue which device tip inhibits electrode-to-tissue contact but permits a shielded reaction zone for the saline solution to react with device electrodes of the alternating current circuit device. The electrons move between device electrodes utilizing electron donor and acceptor carriers within the saline solution. A non-ionizing electromagnetic field quanta is produced near the targeted tissue when the device tip is placed next to the targeted tissue and producing electron donor and acceptor carriers associated with charged specie intermediaries formed above baseline dissociation rates of the saline solution. The charged specie intermediaries are moved toward the targeted tissue surface using redox magnetohydrodynamic propulsion. An effect upon the targeted tissue or the saline solution is induced that is therapeutic for treating the targeted tissue.

In one embodiment, the effect is produced by inducing gene expression with energy that is not injury inducing to the targeted tissue. In another embodiment, the effect is produced by inducing superficial extracellular matrix volume contraction. In a further embodiment, the effect is directing charged species intermediaries toward the target tissue. In yet another embodiment, the effect is precision resection of the targeted tissue. In a further embodiment, the precision resection of the targeted tissue is produced by denaturing exposed proteoglycan aggregates of damaged articular cartilage of the targeted tissue using the charged specie intermediaries in the saline solution having an induced pH below an isoelectric point of targeted tissue. In yet another embodiment, the exposed proteoglycan is chondroitin sulfate proteoglycan that resides as aggregates within the inter-territorial matrix at articular surfaces. In yet another embodiment, the charged specie intermediaries created in the saline solution comprise protons.

In yet another embodiment the effect is stirring of the saline solution. For example, the stirring is microfluidic mixing of the saline solution. In yet another embodiment the effect is delivery of a pharmaceutical agent to the target tissue. In yet another embodiment, the effect is extracellular matrix modification. In yet another embodiment, the effect is to upregulate chondrocyte proliferation. Still another embodiment, the effect is gene transcription initiation.

For example, the activated gene is indicative of differentiated chondrocyte function. Further, the gene may be selected from Versican, COL2A1 and HSPA1A. In yet another embodiment, the chondrocyte is a surface chondrocyte from the target tissue. In yet another embodiment, moving the charged specie intermediaries toward the targeted tissue surface is directionalized with a plenum. For example, the plenum has openings through which the charged specie within the saline solution are thrust.

One aspect of one embodiment of the present invention provides for a technology that creates protons through electron acceleration.

Another aspect of another embodiment of the present invention provides a technology that allows for the sequestration of protons to be delivered to tissues.

Another aspect of one embodiment of the present invention provides for a technology that delivers protons within an engineered irrigant for example, the engineered irrigant is both a proton reservoir and delivery vehicle.

Another aspect of one embodiment of the present invention provides an engineered irrigant that produces ion exchanges in tissues for example deliver of protons which interact with biologic tissues, including specific ion flows both into and out of said tissues.

Another aspect of one embodiment of the present invention provides for a system that accelerates electrons that are close to the tissue to be treated and another aspect of an embodiment of the present invention drives creation of engineered irrigants and also stimulates gene expression at safe thresholds by way of non-ionizing electromagnetic fields. For example, using a high charge/mass ratio (like electrons, but could be any other such high charge/mass ratio elements) enables the use of low energy requirements, increasing safety. This produces useful irrigants having properties sufficient to modify diseased tissue as well as safe stimulation of appropriate ion-targeted gene expression.

Another aspect of one embodiment of the patent invention provides for using normal tissue assembly and repair mechanism, like homeostatic mechanisms, through gene expression, for targeting threshold responsiveness mechanisms at a safe level just above micro-environmental noise. A system and method of one embodiment of the present invention takes advantage of the normal tissue mechanisms which are universal at this safe responsiveness level through electromagnetic fields. Another aspect of the embodiment of the present invention provides for utilizing non-ionizing electromagnetic energy which is not detrimental to cells. It is known that too much electromagnetic energy, like ionizing electromagnetic energy of plasma systems, is detrimental to cells. Non-ionizing electromagnetic energy uses safe forces to effect gene expression. The effects at low threshold responsiveness levels characterize normal homeostatic and tissue repair/assembly mechanisms.

Tissue rescue medical device systems, such as a medical device sometimes referred to herein as a physiochemical scalpel, deploy alternating current redox magnetohydrodynamics within media replacement solutions to produce protonating engineered irrigants designed to disaggregate exposed damaged interstitial matrices through molecular cleavage planes not protected from that irrigant by surface confined assemblies. This targeted molecular disaggregation prepares damaged tissue for mechanical removal by surgically blunt shear forces produced by the device edge to create a healthy lesion site devoid of damaged tissue. Because boundary conditions display a kinetic friction coefficient that is invariant relative to factors that influence formation of a fluid film, such as sliding velocity and axial load, the mechanical implement design for articular cartilage limits its function to low contact speed and pressure loading to yield a kinetic friction coefficient safe for exposed boundary lubrication regimes. Since increased surface asperities suppress the formation of surface-confined assemblies by decreasing interstitial matrix surface hydrophobicity, a condition that impairs wound healing behaviors, re-establishing surfaces devoid of damaged tissue decreases surface roughness so that surface hydrophobicity is increased to a more normal level (i.e. for articular cartilage, a contact angle approximating 105°) supportive of and associated with the capacity to build and maintain surface-confined assemblies.

The trait-targeting dynamics during saline solution media replacement treatment conditions between surface-confined nanoscale assemblies and alternating current redox magnetohydrodynamic tissue rescue procedures as deployed for commonly encountered articular cartilage lesions exhibiting increased surface asperities are discussed herein. As each creates and maintains an electrochemical voltage potential during treatment, tissue rescue is conceptualized as a biophysical battery circuit that deploys capacitive balancing as a trait-targeting mechanism.

Tissue surfaces display a complex tribochemical interfacial system that integrates phase-state transitions between ambient media and differentiated interstitial matrices. Tissue surface-confined assemblies are germ cell independent systems rooted in a foundation of self-assembling amphiphilic bioaggregates which emerge in situ to manage tissue boundaries intrinsic to interfacial venues at which juxtaposed tissue surfaces reside. This system enables solubilization of solid tissue surfaces by transforming the hydrophobic surface of normal interstitial tissue matrices toward a hydrophilic character. To mitigate the high surface hydrophobicity of articular cartilage interstitial matrices (due to very low cell-to-matrix ratios) and their rheologic chemomechanical loading requirements, these assemblies are considered to consist of multiple oligolamellar hydrophilic bimolecular layers ranging between 6-10 nm each and conceptualized as a large three-dimensional reverse micelle approximating 450 nm in thickness. These layers absorb and hold water within their charged core in the manner of hydrophilic lamina with a strong laterally bonded network exhibiting both lipid mobility and viscous resistance. The amphiphilic components are integrated onto solid-liquid surfaces as surfactants in order to modify the interfacial wetting behavior and free energy of hydrophobic interstitial matrices, allowing boundary water to spread into a surface biofilm state rendering the surface more hydrophilic. As the water content of this layer fluctuates during perturbation, amphiphilic components migrate to reduce surface tension and avoid hydrophobic adhesion. Surface-confined assemblies function to protect underlying interstitial matrices from physiochemical perturbation and like other surfactants are often non-uniform in thickness, discontinuous, or can deposit in an island form dictated by surface geometry and interfacial energy conditions. Because they have been shown to replenish by self-assembly mechanisms through surface loading at healthy tissue matrix sites or through native lubricant component delivery, surface-confined assembly mechanisms suggest a tissue homeostatic and repair role that is related to their stability and durability as evident in other tissue types. By serving as an occasional sacrificial layer that is subsequently reconstituted as a means to help mitigate certain perturbation events, the ability to restore tissue surface properties after removing the bioburden of damage tissue that suppresses surface-confined assembly formation and maintenance remains an important wound healing approach.

Because pH (consider the robust charge barrier of the gastric mucosa which exhibits similar surface-confined assembly behavior. Because pH is a useful in situ measure of electrochemical voltage potential, it can be monitored by practitioners in order to titrate the delivery of protic solvents during treatment) can affect the wettability, frictional coefficient, swelling, contact angle hysteresis, and interfacial energy associated with surface-confined assembly behavior, intrinsic amphiprotic properties allow active acid-base equilibria maintenance and stabilization of ambient charged species. In so doing, surface-confined assemblies function as a charge barrier that can modulate osmotic drive energy and interstitial biphasic fluid movement during perturbation, ultimately serving as a link between tribological and mechanical regimes during physiologic conditions. This charge barrier, because of its amphiprotic properties, has been shown to be protective of underlying interstitial matrices during the physiochemical loading, such as ambient protonation potentials, delivered by tissue rescue surgical procedures. In these settings when polar replacement media like saline solutions are utilized to express boundary conditions so as to delineate abnormal surface asperities, surface-confined assemblies induce formation of an additional longer-range charge barrier mechanism with energy storage properties. As an attribute of water residing adjacent to hydrophilic biosurfaces, an ordered-water molecular zone contiguous to surface-confined assemblies forms within which thermal and density gradients do not blend freely. This zone forms rapidly to a thickness of 100-300 μm (even with the mechanical turbulence of vigorous stirring, such as that which occurs during endoscopy, this zone is not eliminated but has been shown to decrease in size), excludes solutes like salts, and is mechanically less mobile due to its crystalline-like architecture. This zone demonstrates electrochemical voltage potentials between 100-200 mV such that the zone is negatively charged and balanced by a region of increased proton concentration within the contiguous bulk water solution. This charge separation proton gradient is a non-thermal process that occurs by absorbing incident interfacial energy to augment the natural water dissociation processes. Because surface-confined assemblies create a hydrophilic surface upon which this proton gradient veneer is formed, this zone supplies a source of stored interfacial energy as a protonation potential during saline media replacement.

The technique of alternating current redox magnetohydrodynamics involves positioning localized alternating current circuits in saline solutions containing electroactive species to move electrons between device electrodes utilizing electron donor and acceptor carriers within host media replacement fluid. This electron transport produces fuel cell like reversible redox reaction pairs associated with charged specie intermediaries formed above baseline solution dissociation rates upon which the attendant alternating current non-ionizing electromagnetic field quanta influence the reaction dynamics. These influences include charged fluid acceleration that create magnetohydrodynamic propulsive thrust currents adapted for medical therapeutics as irrigants. These "irrigants within water" are comprised of regional structure altered molecular water exhibiting differential charged specie separation that results in a sequestered energy source contained within the irrigant that is useful for surgical work.

Alternating current electron movement produces a repetitive molecular energy conversion loop fuel cell in saline solutions involving salt bridge catalyzed splitting and reconstitution of the water molecule. The thermochemical redox reaction pair can be represented as $$\alpha H_2O_{(l)} + \beta XCL \overset{energy}{\longleftrightarrow} (\alpha-\beta)H_{2(g)} + \frac{(\alpha-\beta)}{2}O_{2(g)} + \beta HCl_{(aq)} + \beta XOH_{(aq)} \quad (1)$$

$$(\gamma-\delta)H_{2(g)} + \frac{(\gamma-\delta)}{2}O_{2(g)} + \delta HCl_{(aq)} + \delta XOH_{(aq)} \overset{energy}{\longleftrightarrow} \gamma H_2O_{(l)} + \delta XCl_{(s)} + \Delta \quad (2)$$

with the variables α, β, γ, and δ as the molar quantities that satisfy the oxidation reduction requirements for the overall reaction set and Δ as the available heat and/or electrical energy. Attendant non-ionizing electromagnetic field quanta influence this redox reaction pair to move reactant and product charged species formed above baseline solution dissociation rates away from the device electrodes and directionalized by a plenum. As regional proton concentration differentials increase above normal solution dissociation rates due to the magnetohydrodynamic pumping mechanism, an electrochemical proton gradient develops from the resultant charge separation, creating an irrigant with energy storage properties similar to that created by surface-confined assemblies during saline media replacement. This energy source is maintained during device activation and delivered to tissue surfaces as a protonation potential below the isoelectric point of exposed damage interstitial matrices. The protonation potential is delivered in the form of a protic solvent that balances proton delivery with sensible thermal contributions typical of acute wound healing exudates. In so doing, the irrigant battery energy is consumed by the exposed negative charge density of damaged interstitial matrices leading to molecular disaggregation useful for eliminating damaged interstitial matrix tissue.

Proton gradients are a common biologic mechanism utilized to generate electrochemical potential in order to convert and store energy. Regardless of their generation mechanism, by depicting proton gradients as electrochemical cells, their electrical polarity can be represented as a unidirectional flow of electric charge suitable for direct current modeling. For example, biologic membrane-based proton gradients such as in mitochondria and chloroplasts can be depicted as − ‖‖+ because these gradients require a physical membrane structure to maintain charge separation after charge movement. Likewise, ‖ − + can represent a proton gradient that forms adjacent to hydrophilic tissue surfaces such as that generated by surface-confined assemblies during saline media replacement; and, − + can represent protonating irrigant gradients that form within solutions without physical structures to maintain charge separation such as those generated by alternating current redox magnetohydrodynamics. In each instance, and although generated by different mechanisms, these proton gradients serve as energy conversion systems generated from electron transport between charge carriers to create protonation potentials. Consequently, each proton gradient electrochemical cell is capable of direct current discharge of its protonation potential which can be represented in a battery circuit.

Because surface-confined assemblies form and maintain a proton gradient veneer when confronted with saline solution media replacement, and because boundary conditions are dominated by chemistry, alternating current redox magnetohydrodynamics was chosen for tissue rescue because a similar proton gradient can be design formulated within the same saline solution and delivered in situ as a trait targeting mechanism for areas of abnormal surface asperities associated with absent surface-confined assemblies. Accordingly, trait-targeting energy can be modeled as a direct current supercircuit represented by instantaneous voltage energy transfers using the water molecule as an energy transducer. During tissue rescue, a proton gradient is formed that is delivered to tissue surfaces, much like a portable battery, and discharged as a protonation potential. Because the intermolecular hydrogen bond stretching frequencies of water demonstrate a proton based femto- to pico-second oscillation period, electron movements associated with alternating current polarity changes are less rapid so that water protons in the irrigant experience direct current forces ($10^{12-15}$ Hz oscillation rate versus $10^{5-6}$ Hz circuit frequencies) during device activation. Accordingly, irrigant batteries generated through motive proton delivery gradients can be reduced to a direct current energy storage model capable of direct current discharge during contact with a specific therapeutic target. Viewed historically, these intramolecular dynamics are analogous to a full-wave bridge electrolytic rectifier that converts an alternating current into a direct current except that redox magnetohydrodynamics produce a steady direct current electrochemical voltage potential from the rectified alternating current supply without using a smoothing reservoir capacitor, capacitor-input filter, or voltage regulator. During tissue rescue, the irrigant battery interacts with the tissue battery generated by surface-confined assemblies.

Normal tissue surface-confined assemblies create a hydrophilic substrate upon which a proton gradient veneer forms during saline solution media replacement. In this setting, an electrochemical circuit can be conceptualized as a direct current model of retained voltage potential with intact surface-confined assemblies serving as an insulator substrate while the electrochemical gradient battery is charged by proton veneer formation mechanisms described above. Viewed in toto for a specific surface-confined assembly geographic island with distinct margins, a single continuous electrochemical cell can be conceptualized as participating in a battery circuit and which retains a protonation potential capable of discharge.

Because damaged tissue surfaces lack surface-confined assemblies and therefore the formation of a proton gradient veneer, the exposed interstitial matrix constitutes an abnormal hydrophobic region that presents its negative charge density to the treatment venue. This exposed negative charge density separates surface-confined assembly islands through edge contact angle hysteresis with the damaged tissue surfaces acting as an electrical ground. This ground leads to discharge of adjacent tissue surface electrochemical cells as a protonating force upon the negatively charged exposed tissue. This protonation potential discharge facilitates molecular disaggregation of damaged interstitial matrices that already exhibit deteriorating surface-layered shear properties of collagen fibril disruption and orientation changes, weak collagen-to-proteoglycan bonds, proteoglycan and lipid depletion, aberrant water content, and decreased fixed charge density. This disaggregation leads to a decrease in surface roughness that can lead to an increase in surface hydrophobicity toward a level capable of building and maintaining surface-confined assemblies necessary to facilitate increased wettability, more normal chemomechanotransductive environments for subadjacent tissue, and unburdened tissue homeostatic and repair mechanisms. This biopolymer disaggregation process mimics the brining effects on damaged tissue of acute wound healing exudates.

At damaged tissue sites that exhibit a level of surface roughness which cannot be disaggregated by the protonating discharge of adjacent surface-confined assembly batteries alone during saline media replacement, tissue rescue procedures deliver an engineered irrigant protonation potential that is capacitance balanced and with reverse polarity to that generated by surface-confined assemblies at normal tissue surfaces. The technique of capacitance balancing between the irrigant and tissue surface batteries is used so that varied capacitance between the two energy sources does not lead to significant discharge of either during treatment. By designing the irrigant battery with a capacity similar to the tissue surface battery, the reverse polarity delivery is a safe targeting force because the engineered irrigant is very portable within saline media replacement venues. The magnetohydrodynamic propulsive force easily interrupts the interfacial discharge of adjacent tissue surface protonation potentials and concentrates a larger protonation potential at the exposed negative charge density of the damaged interstitial matrices. This therapeutic process mimics the protic solvent generated by enhanced azurophilic degranulation of polymorphonuclear neutrophil granulocytes during the early phases of acute wound healing.

At sites where normally juxtaposed tissue surfaces require relative motion, surface-confined nanoscale assemblies form in situ as functional integrators to manage the hydrophobic interfacial character and differentiated behavior of interstitial matrices. Once surface areas become damaged and exhibit abnormal asperities exceeding the capacity of intrinsic homeostatic and repair mechanisms, surface hydrophobicity decreases to a state upon which surface-confined assemblies cannot form or be maintained; a condition of interfacial dysfunction leading to altered chemomechanotransductive environments for and provocation toward further pathologic phenotypic shifts in subadjacent tissue. The bioburden that such damaged tissue represents is related to its clearance potential; and, in settings of limited or acquired clearance deficiency, wound bed preparation remains an important therapeutic endeavor. For this reason, trait-targeting interventions have been designed to afford practitioners the ability to create an healthy wound bed when intrinsic homeostatic and repair capacities may be overwhelmed. By mimicking the important mammalian wound healing behavior of distinguishing between normal and damaged tissue surfaces based upon the presence or absence of surface-confined assemblies, the removal of damaged tissue associated with abnormal surface asperities decreases surface roughness so that surface hydrophobicity can be increased to more normal levels, producing conditions favorable to surface-confined assembly nucleation, reformation, growth, and maintained lesion site coverage. By creating a healthy wound bed unencumbered by damaged tissue, the re-establishment of interfacial regimes upon return to native environments post-treatment can restore conditions supportive of differentiated function, including intrinsic homeostatic and repair capacities, in subadjacent tissue.

The bioburden clearance potential for many damaged interstitial matrix surfaces is augmented by the formation of acute wound healing exudates when intrinsic homeostatic and repair capacities are not adequate. These exudates precondition damaged tissue toward a state amenable for removal by mechanisms like phagocytosis. This preconditioning is brought about by protic solvents, such as those generated through azurophilic degranulation of polymorphonuclear granulocytes during the acute phases of wound healing, that are primarily responsible for biopolymer disaggregation of damaged tissue present in a wound bed. Because the rheologic requirements of normally juxtaposed tissue surfaces can create challenges for establishing acute wound healing exudates and localization of associated cellular complements, this clearance potential limitation above intrinsic homeostatic and repair mechanisms has been advanced as one reason why some differentiated tissue surfaces have been linked with a reputation for poor healing capacity. Alternating current redox magnetohydrodynamic technology has been adapted for surgical applications to address this clearance deficiency by imitating the protic solvent component of acute wound healing exudates to produce biopolymer disaggregation of exposed damaged tissue not protected by surface-confined assemblies (exposed damaged tissue, often characterized as surface fibrillation due to its collagen content, exhibits deteriorating surface-layered shear properties of collagen fibril disruption and orientation changes, weak collagen-to-proteoglycan bonds, proteoglycan and lipid depletion, aberrant water content, and decreased fixed charge density that is a suitable biopolymer disaggregation target for protic solvents not strong enough to overcome the normal subadjacent tissue makeup at the wound bed periphery. In this manner, the physiochemical scalpel can produce a healthy wound bed without altering cell viability or residual differentiated function). By adapting alternating current redox magnetohydrodynamics, the advantages of protic solvents can be delivered as engineered irrigants without the disadvantages of full enzyme system deployment typically associated with azurophilic degranulation such as myeloperoxidase and nicotinaminde adenine dinucleotide phosphate oxidase systems.

By using various saline media replacement formulations during endoscopic procedures to express boundary conditions at normal sites, surface-confined assemblies display tribological and mechanical working properties governed by interfacial chemistry and a kinetic friction coefficient invariant to perturbations effecting fluid film formation, respectively. Capacitance balanced engineered irrigants controllably deliver protonation potentials appropriate for boundary condition interfacial chemistry in order to precondition damaged tissue for removal. The energy transduction processes of protonation coupled conformational dynamics has been shown to achieve nanometer resection precision through a guest chemical denaturization process below the isoelectric point of exposed damaged interstitial tissue matrices. This energy transduction process utilizes low stability protonating agents involved in exothermic tissue homeostasis and repair mechanisms through disproportionation redox reactions like those produced by the respiratory burst myeloperoxidase system activated by azurophilic degranulation of polymorphonuclear neutrophil granulocytes during the acute phases of wound healing. Rather than relying upon local phagocytic-like processes as in acute wound healing behaviors, once preconditioned, damaged tissue is removed by physical implements of the device system appropriate for treatment interfacial mechanical conditions through shear débridement and flushed away by the saline media solution. Preconditioning and removal of damaged tissue in this manner has been a successful acute wound healing biomimic to produce a healthy wound bed and assist differentiated biosynthetic tissue assembly activities in subadjacent tissue.

Although the deterioration of hydrophobicity associated with surface roughness can be responsible for the absence of surface-confined assemblies at damaged sites, changes in interfacial energy and composition of synovial fluid likely play important complementary roles. As a manifestation of interfacial dysfunction, the inability of surface-confined assemblies to build on damaged tissue surfaces may relate to pressure-to-surface area dependent gas-gap alterations, exposed interstitial matrix negative charge density effecting hydrogen bond alterations in interfacial water, or cavitation erosion associated with wear particles not captured by innate removal mechanisms. As discussed herein, and as in other tissue types for which irrigants effect surface roughness, the protonation potentials generated by saline media replacement that self-target exposed interstitial matrices by adjacent interfacial energy discharge have been observed clinically during endoscopy at articular cartilage surfaces for many decades. The simple observation that surface fibrillation characteristics change with different replacement media provides an important clue to the clearance potential that can be augmented by engineered irrigants through targeted biopolymer disaggregation. This disaggregation of exposed fibrillated tissue bathed in saline solutions accentuates the distinction between normal and abnormal surfaces and the resultant preconditioning remains a very plausible mechanism explaining the clinical improvements observed with arthroscopic lavage. Increased protonation potentials likewise have been demonstrable within synovial fluid alterations that occur commensurate with disease; altered synovial fluid composition in these instances manifests as a large endogenous wound exudate delivering increased protonation potentials when damaged tissue removal is required. By preconditioning damaged surface tissue to facilitate removal, disaggregated debris by increased synovial fluid protonation potentials can be delivered to the long-known mechanisms of synoviocyte phagocytosis.

For articular cartilage, older technologies enabling palliative tissue resection have been deemed inappropriate for wound healing because of unavoidable volumetric and functional over-resection that simply expanded lesion size, eliminated structurally stratified healing phenotypes, and left a residual damaged tissue surface in no way suitable for the nucleation, reformation, growth, or maintenance of surface-confined assemblies. Concerns that such palliative approaches provoke disease progression have understandably led to reconsideration as to whether these treatments provide any benefit toward wound site bioburden control even when used only to achieve short-term symptomatic relief. While articular cartilage has shown many of the wound healing behaviors associated with homeostatic and repair activity at its surfaces, it is unable to remove macroscopic damaged tissue from its surface in any meaningful way. This clearance deficiency is largely due to the unique avascular structural transport properties and synovial environment of articular cartilage, both of which alter typical inflammatory processes and the ability to localize effective wound healing exudates aside from altered synovial fluid composition when viewed as a form of wound exudate. Because an effective clearance process is important during the acute phases of wound healing, this deficiency has frustrated the efforts to create a healthy lesion site widely considered important for both primary and secondary intention articular cartilage wound healing.

Similar to the fundamental cancer observation that abnormal cell growth kinetics could serve as a therapeutic trait-targeting substrate to preserve healthy tissue and enable substantial disease burden mitigation, surface-confined nanoscale assemblies are likewise providing this opportunity for conditions like osteoarthritis. Although homeostatic and repair capacities may be decreased in areas surrounding diseased articular cartilage as in other tissue types, partial thickness lesions by definition contain viable cells and residual tissue function so that creating conditions favorable to the responsive capacity of subadjacent tissue allows that tissue the opportunity to mount unencumbered differentiated homeostatic and repair responses. For juxtaposed tissue surfaces requiring relative motion such as articular cartilage, a therapeutic focus upon partial-thickness lesion wound healing by secondary intention will likely augment recent approaches studying primary intention wound healing as applicable to full thickness lesions; understanding interfacial behavior can better enable tissue surface host-to-implant integration and reconstruction of suitable surface wear properties. Secondary intention wound healing approaches, while typically dependent upon exudative processes, seek preserved subadjacent tissue because of tissue loss that occurs with damage. While assisting the limited or acquired clearance deficiency, alternating current redox magnetohydrodynamics has been shown to achieve other important secondary intention wound healing effects, including wound bed contraction that increases cell/matrix enrichment ratios and induction of tissue assembly responses accessing genomic control mechanisms, useful to provocate post-treatment wounding healing as interfacial properties are re-established toward a better bearing surface.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 7A-F illustrates a medical device according to one embodiment of the present invention with an alternating current redox magnetohydrodynamic proton pump producing an irrigant within water engineered for treating targeted tissue.

DETAILED DESCRIPTION OF THE INVENTION

Definitions

Figure 1:
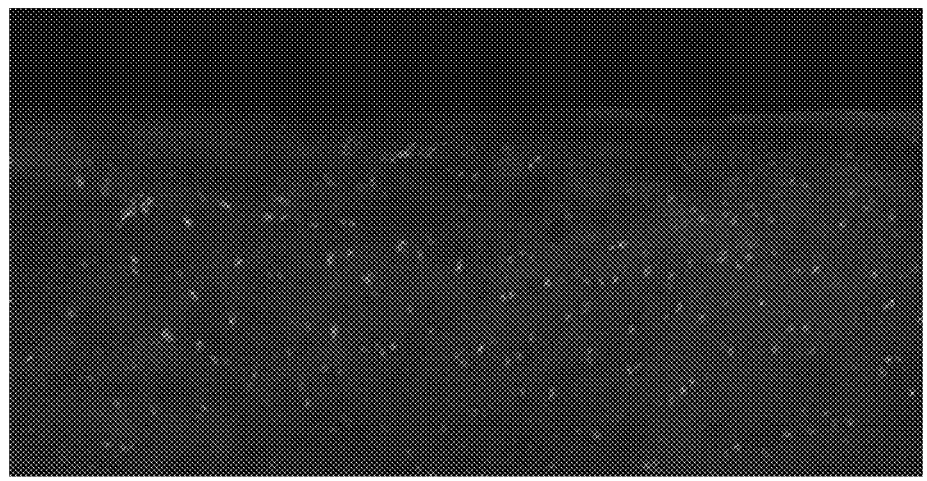
FIG. 1 illustrates a representative post-treatment integrated Live/Dead cell viability stain section image demonstrating viable chondrocytes.

The following definitions are used herein unless a symbol is defined differently in the context of a specific use, paragraph or equation.

As used herein "a" means one or more.

As used herein "Δp" is chemiosmotic potential.

As used herein "F" means Newtonian Force, measured in Newtons (N) for this exercise. Recall that $$1N = 1\frac{kg*m}{s^2}.$$

As used herein "Q" means electrical charge of a particle, direction and magnitude depending on valence. Measured in Coulombs (C).

As used herein "E" means electrical potential, measured in Volts/meter $$\left(1V = 1\frac{N*m}{C}\right).$$

As used herein "υ" means measured in meters/second $\frac{m}{(s)}$.

As used in an equation "a" means measured in meters/second² $\frac{m}{(s^2)}$.

As used herein "F=Q*(E+υ×B)" means the force of a particle is equal to the product of the charge of that particle (Q) and the sum of the electrical field (E) and the cross product of the velocity of the particle (υ) and the magnetic field (B).

As used herein "F=m*a" means the force on an object is equal to the product of the mass and the object's acceleration.

As used herein "V=I*R; P=VI" means Ohm's law and the power law.

As used herein "$m_e$" means 9.109×10⁻³¹ kg. Periodic Atomic weight (g/mol) divided by Avagodro's Number (6.022×10²³).

As used herein "$m_H$" means 1.67×10⁻²⁷ kg. Periodic Atomic weight (g/mol) divided by Avagodro's Number (6.022×10²³).

As used herein "$m_O$" means 2.66×10⁻²⁶ kg. Periodic Atomic weight (g/mol) divided by Avagodro's Number (6.022×10²³).

As used herein "$m_{OH}$" means 2.83×10⁻²⁶ kg. Sum of mass of O+Hydrogen.

As used herein "$m_{Na}$" means 3.82×10⁻²⁶ kg. Mass of a sodium ion in saline solution.

As used herein "$m_{Cl}$" means 5.89×10⁻²⁶ kg. Mass of a chloride ion in saline solution.

As used herein "Q" means (+/−) 1.60×10⁻¹⁹ C. Single unit of charge.

An inverse mass ratio battery (IMRB) may be used to accomplish various tissue rescue treatments which include but are not limited to precision resection; microfluidic mixing, stirring, and pumping; facilitative colloidal crystal, hydro- and sol-gel self-assembly; electrolyzable interfacing agent modification; charged species injection and migration; electromagnetic induction coupling; electro-wetting, -formation, and -swelling; micelle and coascervate formation; pharmaceutical agent delivery; electromagnetic phoresis; extracellular matrix modification; and biosynthetic transcription initiation. Tissue surface based medical conditions using well established endoscopic access procedures that utilize saline solutions comparable to that within which biologic tissue resides will benefit from a system and method as disclosed herein.

One embodiment of the present invention utilizes an IMRB which is an energy source generated in situ during treatment by inducing charged specie separation in saline solutions through an energy conversion process patterned after common biologic electron transport chain mechanisms that form proton gradients. According to one method for treating targeted tissue, localized alternating current circuits are positioned in saline solutions containing electroactive species to move electrons between device electrodes utilizing electron donor and acceptor carriers within the host fluid. This electron transport produces fuel cell like reversible redox reaction pairs associated with charged specie intermediaries formed above baseline solution dissociation rates. The reaction dynamics are influenced by the attendant alternating current non-ionizing electromagnetic field quanta.

These influences include charged fluid acceleration that create magnetohydrodynamic propulsive thrust currents. Although traditionally used to propel the originating source, by changing the observational reference frame, the thrust currents are adapted for medical therapeutics as irrigants. These "irrigants within water" are comprised of regional structure altered molecular water exhibiting differential charged specie separation that results in a sequestered energy source contained within the irrigant that is useful for surgical work. Because biologic tissue resides in a saline solution milieu redox magnetohydrodynamic phenomena have been deployed to alter these solutions to create motive delivery gradient originating from a medical device.

It is thought that the energy conversion process from electron transport to charged specie separation within the attendant non-ionizing electromagnetic environment is governed by the charge-to-mass ratio (Q/m) profile of saline solution constituents whereby those species with the highest Q/m generally travel furthest in host media. In one example, the IMRB is generated from NuOrtho Inc.'s Engineered Irrigants™ solutions. IMRB may be generated by a proton gradient formed in saline solutions which predominantly contain charge equivalent monovalent anions and cations. For instance, sodium (or potassium) chloride solutions contain predominantly Cl⁻, OH⁻, Na⁺ (or K⁺), H⁺, and H₃O⁺ for which the charge magnitude of the Q/m ratio is eliminated during differential charge specie separation analyses of alternating current redox magnetohydrodynamic phenomena. This elimination enables the design formulation of irrigant differential charge specie movement to be based upon mass only, a feature that led to these energy sources being designated as IMRB.

Referring now to one embodiment of the present invention, a physiochemical scalpel that functions as an alternating current redox magnetohydrodynamic proton pump form of energy sequestration is utilized which maintains regional proton gradients within the saline solutions ambient to biologic tissues. Referring now to FIG. 7A-F, the creation of an irrigant engineered in saline solutions useful in the IMRB is illustrated according to one embodiment of the present invention. Static images obtained from digitized videography are depicted from left to right at 0 Watts; 25 Watts; 50 Watts; 75 Watts; 100 Watts; 120 Watts. Note that early non-soluble gas (bubble) production does not begin until 35 W after which the non-soluble gas production level remained consistent without overwhelming the dynamics of the primary reaction zone until 75 W when the turbulence and mass effect of the increased gas production facilitated the removal of the reactants products from the primary reaction zone more dramatically. Because the intermolecular hydrogen bond stretching frequencies of water demonstrate a proton based femto- to pico-second oscillation period, electron movements associated with alternating current polarity changes are less rapid so that water protons in the irrigant experience direct current forces ($10^{12-15}$ Hz oscillation rate versus $10^{5-6}$ Hz circuit frequencies) during device activation. Accordingly, irrigant batteries generated through motive proton delivery gradients can be reduced to a direct current energy storage model capable of direct current discharge during contact with a specific therapeutic target.

Alternating current (AC) electron movement produces a repetitive molecular energy conversion loop fuel cell in saline solutions involving salt bridge catalyzed splitting and reconstitution of the water molecule. The thermochemical redox reaction pair can be represented as $$\alpha H_2O_{(l)} + \beta XCL \overset{energy}{\longleftrightarrow} (\alpha - \beta)H_{2(g)} + \frac{(\alpha - \beta)}{2}O_{2(g)} + \beta HCl_{(aq)} + \beta XOH_{(aq)} \quad (1)$$

$$(\gamma - \delta)H_{2(g)} + \frac{(\gamma - \delta)}{2}O_{2(g)} + \delta HCl_{(aq)} + \delta XOH_{(aq)} \overset{energy}{\longleftrightarrow} \gamma H_2O_{(l)} + \delta XCl_{(s)} + \Delta \quad (2)$$

with the variables $\alpha$, $\beta$, $\gamma$, and $\delta$ as the molar quantities that satisfy the oxidation reduction requirements for the overall reaction set and $\Delta$ as the available heat and/or electrical energy. Attendant non-ionizing electromagnetic field quanta influence this redox reaction pair to move reactant and product charged species formed above baseline solution dissociation rates away from the device electrodes and directionalized by a plenum. Without reconciling reference frame transformations, when charged species move in electric and magnetic fields, the following two laws apply, the Lorentz force and Newton's second law of motion, which can be equated as follows $$F = Q(E + v \times B) \quad (3)$$

$$F = ma = m\frac{dv}{dt} \quad (4)$$

$$\left(\frac{m}{Q}\right)a = E + v \times B \quad (5)$$

Where, for equation lines (3), (4) and (5), F is the force applied, E is the electric field, B is the magnetic field, t is time, and v, m, a, Q are the velocity, mass, acceleration, and charge of the species, respectively.

In examining the molecular dynamics of an irrigant proton transport gradient that results in energy sequestration, the intermolecular hydrogen bond stretching frequencies of water allow system treatment as a direct current model. As such, the low magnetic field curl component (v×B) in this system (alternating current redox magnetohydrodynamic systems deploy electromagnetism rather than permanent magnetism as utilized in other magnetohydrodynamic system configurations; therefore, the magnetic component can be varied based upon the amount of electric current or duty cycle utilized. Depending upon the generator energy configuration required for particular device system goals, the magnetic curl component can be inconsequential to treatment venue, or in other instances, can induce therapeutic eddy currents requiring mixed modeling techniques), which is principally orthogonal to the electromotive force, can be condensed so that charged specie movement is reduced to a single dimension model see for example FIG. 8.

Figure 8:
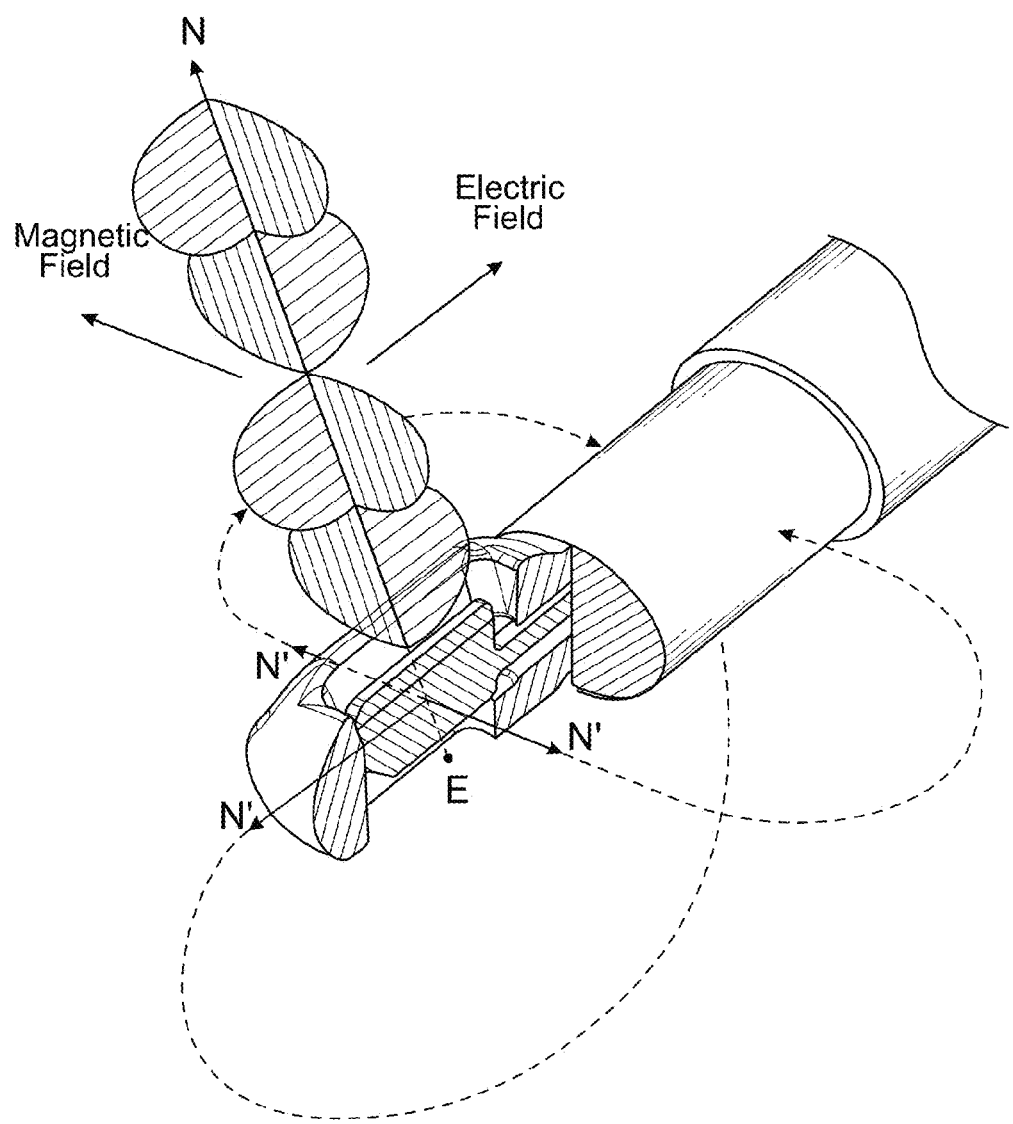
FIG. 8 illustrates a poynting vector demonstrating field-force summations.

Referring now to FIG. 8, representative Poynting vector illustration demonstrating field-force summations. Magnetohydrodynamic propagation forces $\vec{N}$ are applied to working fluids that enters a device plenum according to one embodiment of the present invention at point E so that charged specie and host fluid carrier momentum thrusts in the exit direction of the plenum opening face. The vector field lines N' depict overall trajectories due to charge density variances between the electrode edge versus its face. Note that the angular momenta and associated torque force densities about the propagation axis are not shown. The plenum opening egress/ingress dimension area ratio as depicted is 2.16.

By equating charged species acceleration and distance traveled $$a = \frac{QE}{m} \quad (6)$$

$$d = at^2 \quad (7)$$

$$d = \frac{QE}{m}t^2 \quad (8)$$

the relative scale travel distance between two different charged species, x and y, can be depicted as $$\frac{d_x}{d_y} = \frac{\frac{Q_x E t^2}{m_x}}{\frac{Q_y E t^2}{m_y}} \quad (9)$$

Since Q, E, and t are the same for x and y as charge equivalent monovalent species, during reactions (1) and (2), relative scale travel distances for can be represented as the inverse mass ratio defined as $$\frac{d_x}{d_y} = \frac{m_y}{m_x} \quad (10)$$

Table 1 presents inverse mass ratios of predominant charged species in a sodium chloride solution reflecting the formation of a proton gradient based upon differential charged species movement.

As regional proton concentration differentials increase above normal solution dissociation rates due to the magnetohydrodynamic pumping mechanism, an electrochemical gradient develops from the resultant charge separation. In settings like this wherein protons are available for movement, pH is a useful in situ measure of electrochemical potential as it can be monitored by practitioners in order to titrate effect during treatment.

Figure 9:
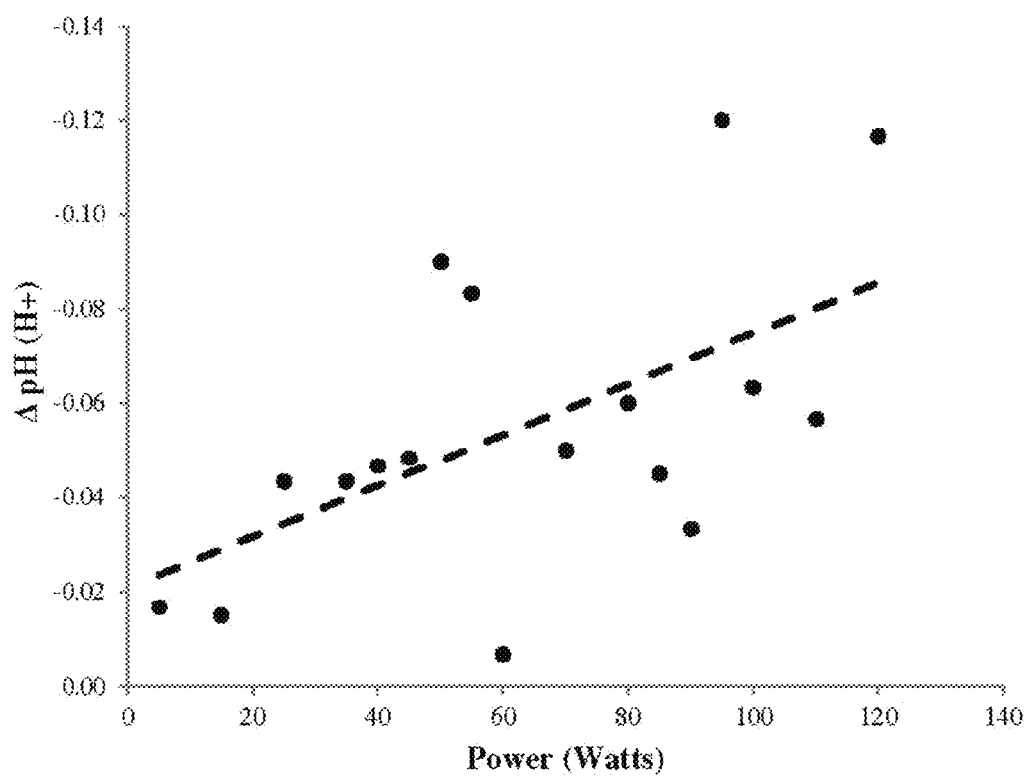
FIG. 9 illustrates an electrochemical potential versus power delivery.
Figure 10:
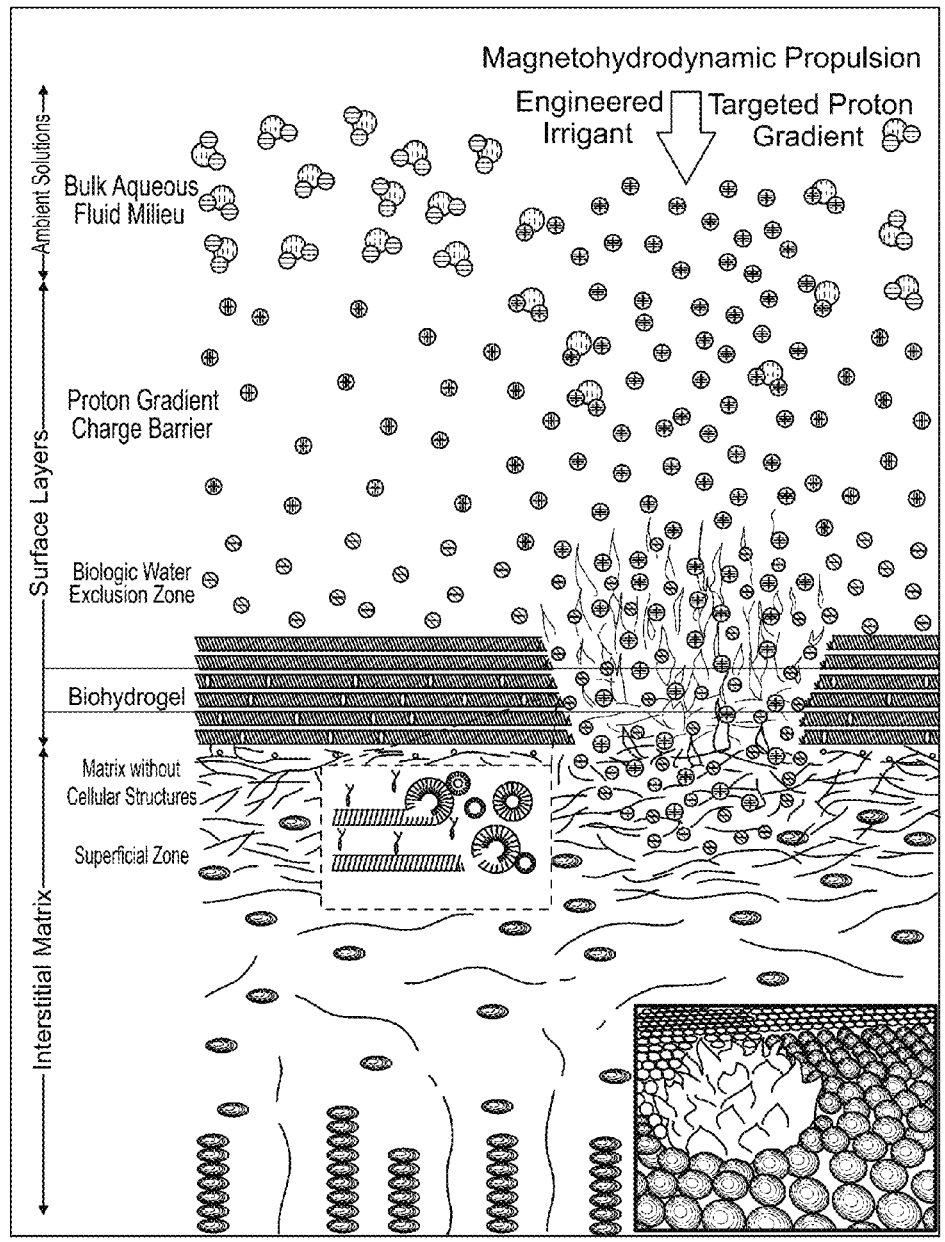
FIG. 10 illustrates an artistic illustration of biologic trait-targeting for a geographically contained tissue surface based lesion.

Referring now to FIG. 9, experimental data of irrigant electrochemical potential versus power delivery as a function of pH is illustrated. $R^2=0.311$; $p<0.02$. The goodness-of-fit linear regression is better for the segment during which low level non-soluble gas formation occurs (35-75 W) with increasing scatter as primary reaction zone turbulence increases within the device plenum and that $R^2$ values can be varied based upon plenum architectural design. Data from sodium chloride solutions (300 mOsm/L) at 20° C. with alternating current from 5 to 120 W with an 8500 V peak-to-peak setting (4250 peak voltage) and 390 kHz damped sinusoid bursts with a repetition frequency of 30 kHz into 500 ohms. Because the electrochemical potential is representative of differential charged specie separation and directly correlates with power delivery, in situ measures of pH are associated with irrigant energy.

Referring now to Table 1, an inverse mass ratio and relative scale travel distances between predominant charge equivalent monovalent species predominantly present in sodium chloride solutions is illustrated. $N_A$ is Avogadro's number. Comparison between predominant charged species present in the reaction venue during creation of an Engineered Irrigant relative to the $H^+$. Note that the charge valence magnitude of each species is equal so that the inverse mass ratio represents $$\left(\frac{d_x}{d_y}\right);$$

evaluation of an $x^{2+}$ species would require reintroduction of Q.

The proton motive force or chemiosmotic potential that is generated by the proton gradient system is represented as the sum of the pH gradient and resultant voltage potential $$\Delta p = \frac{(-2.303 \, RT \Delta pH)}{nF} + \Delta \psi \qquad (11)$$

and the total Gibbs free energy available from a proton gradient irrigant in an open system is $$\Delta_i G = -2.303 RT \Delta pH + nF \Delta \psi \qquad (12)$$

where R is the universal gas constant ($8.315 \times 10^{-3}$ kJ/mol-K), T is the absolute temperature (° K), n is the number of electrons transferred; F is the Faraday constant (96.48 kJ/V-mol), and $\psi$ is the voltage gradient or voltage potential. Like biologic energy management systems, the relative contributions between the pH gradient ($\Delta pH$) and the voltage potential ($\Delta \psi$) for overall $\Delta_i G$ is specific for particular Engineered Irrigants. For example, in an illustrative treatment setting that generates an irrigant pH gradient of 0.10 and voltage potential of 0.010V at a room temperature of 25° C., the inverse mass ratio battery would yield a free energy change of 0.57 kJ/mol for the maintained pH gradient and 0.97 kJ/mol for the created voltage gradient. Combined, the total 1.54 kJ/mol reflects the $\Delta$ of equation (2) for a particular redox reaction pair conversion loop that generates a proton gradient. For a practitioner who changes the pH gradient from a to b during treatment, $\Delta pH$ is directly proportional to the irrigant $\Delta_i G$ being deployed $$\frac{\Delta pH_a}{\Delta pH_b} = \frac{\Delta_i G_a - nF\Delta \psi_a}{\Delta_i G_b - nF\Delta \psi_b} \qquad (13)$$

A system and method of an embodiment of the present invention employs alternating current redox magnetohydrodynamics thereby eliminating large generator current impulses and minimizing electric current deposition into tissue. These features aid to eliminate the two most common causes of iatrogenic collateral tissue damage. This embodiment is able to capture, direct, position, and move a fluid constituent to tissue surfaces as a therapeutic agent without extended cumbersome channel structures for guidance. The transport is controlled with redox chemistry and which can be turned on and off strategically. The products generated can be flushed away rapidly by the host bulk endoscopic saline solution at the practitioner's convenience. The system for use in therapeutic treatment of targeted tissue and its method of use may be applied to such conditions as osteoarthritis so as to reduce disease burden.

Attendant non-ionizing electromagnetic field quanta superimposed upon alternating current formed charged species is an energy transfer process analogous to common biologic energy management methods whereby oxidation-reduction electron transport chain reactions enable certain charge carriers to pump protons. In most biologic systems, the mechanisms for maintaining proton charge separation are physical membranes or boundary coascervates at which $\Delta pH$ and $\Delta \psi$ may act independently or jointly depending upon the specific transport mechanisms in operation. For example; characteristics perhaps not more clearly demonstrated by the differences between mitochondria and chloroplast membranes. While irrigants engineered via magnetohydrodynamics to maintain charge separation, differences in relative contribution from $\Delta pH$ and $\Delta \psi$ to overall $\Delta_i G$ can be likewise design formulated for specific indications. A significant advantage of the IMRB resides in the simplified design formulation for proton pumping stoichiometry. Charge equivalent monovalent species uniquely relate to the Nernst n in equations (11) and (12) so that the number of protons compared to the number of positive charges moved per electron transported (i.e. monovalent Goldman-Hodgkin-Katz treatment) during the alternating current half cycle more directly correlates with the in situ pH changes that are useful to monitor during treatment. Multivalent species can have a profound effect on the ability to form and discharge a proton gradient. Further, these species also affect tissue surfaces, much like their behavior at the electrical double layer that forms on micro and nanofluidic device surfaces, by altering charge interactions and interfacial energy.

Normal tissue surfaces demonstrate phase-state transition properties. This is akin to this electric double layer, being comprised of a biologic exclusion zone proton gradient formed adjacent to hydrophilic biohydrogel phospholipid oligolamellar layers which manage interstitial matrix wettability and surface charge barriers. Although generated by a different mechanism, the IMRB exhibits similar energy storage features to that of the biologic exclusion zone proton gradient. Irrigants engineered with proton gradient energy is designed to be of similar magnitude to normal tissue surface interfacial proton gradient energy so that varied capacitance between the two energy sources does not lead to significant discharge of either during treatment. These damaged surfaces are devoid of hydrophilic biohydrogel layers because of increased roughness and decreased wettability. Consequently, the biologic exclusion zone proton gradient cannot form appropriately upon the exposed hydrophobic interstitial matrices. In these locations, the IMRB energy is consumed through the fixed negative charge density of the exposed interstitial matrix as a protonating force. Since both the irrigant and interfacial batteries are based upon proton gradients in water which demonstrates fast intermolecular bond oscillation rates, trait-targeting energy can be modeled as a direct current supercircuit represented by instantaneous voltage energy transfers.

As designed for use with a physiochemical scalpel, the IMRB energy capacity is customized to achieve nanometer resection precision through a chemical denaturization process below the isoelectric point of exposed damaged interstitial tissue matrices. This therapeutic process was adapted from a biologic treatment hint offered by polymorphonuclear neutrophil granulocytes; wherein, their respiratory burst myeloperoxidase system produces low stability protonating agents involved in exothermic tissue homeostasis and repair mechanisms through disproportionation redox reactions. Because of high proton motilities in water, stoichiometric protonation $\beta \downarrow (H \downarrow n)$; $\beta_{H_n}$ is the cumulative protonation constant for the addition of the $n^{th}$ proton for the formation of $H_nP$ from $nH^+$ and P, where P is an interstitial matrix protein or polymer complex. The energy transduction processes of protonation (coupled conformational dynamics) is a very rapid charge redistribution process that leads to biopolymer disaggregation through molecular cleavage planes accessible due to normal tissue surface barrier losses and degenerate matrix properties. Irrigant proton recruitment and pressure force modeling for a commonly deployed 25 W alternating current input of one embodiment of the present invention demonstrated the movement of $5.3 \times 10^{11}$ protons per 1.3 µs half period yielding 2.8 mmHg. This protic solvent pressure force is similar in magnitude to the transcapillary net filtration gradient required to generate normal net capillary filtration and facilitates irrigant access into damaged interstitial matrices at an energy level sufficient to chemically denature diseased collagen-proteoglycan matrices and bring about nanometer level resection precision.

One aspect of one embodiment of the present invention provides for resection precision which guards against volumetric and functional over-resection. Over-resection can contribute to disease burden.

Redox magnetohydrodynamic engineered irrigants (transportable regionally structure-altered fluids or water) are based upon constituent charge-to-mass ratio profiles: radiofrequency electromagnetic energy produces a Lorentz force generated proton delivery gradient in saline associated with biologic-appropriate motive forces.

These gradients impact a specific tissue target by locally altering the saline solutions. Engineered Irrigants are created by positioning localized alternating current circuits in saline solutions to produce redox reaction pairs upon which attendant non-ionizing electromagnetic field quanta influence reaction dynamics (see for example FIG. 7). Although charged species, like material particles and ions, generate their own electric and magnetic fields, disclosed herein are systems, methods and examples of irrigants engineered therewith through Lorentzian relative scale modeling of venue-specific charged species based upon useful in situ biologic measures of electrochemical potential.

Figure 11A:
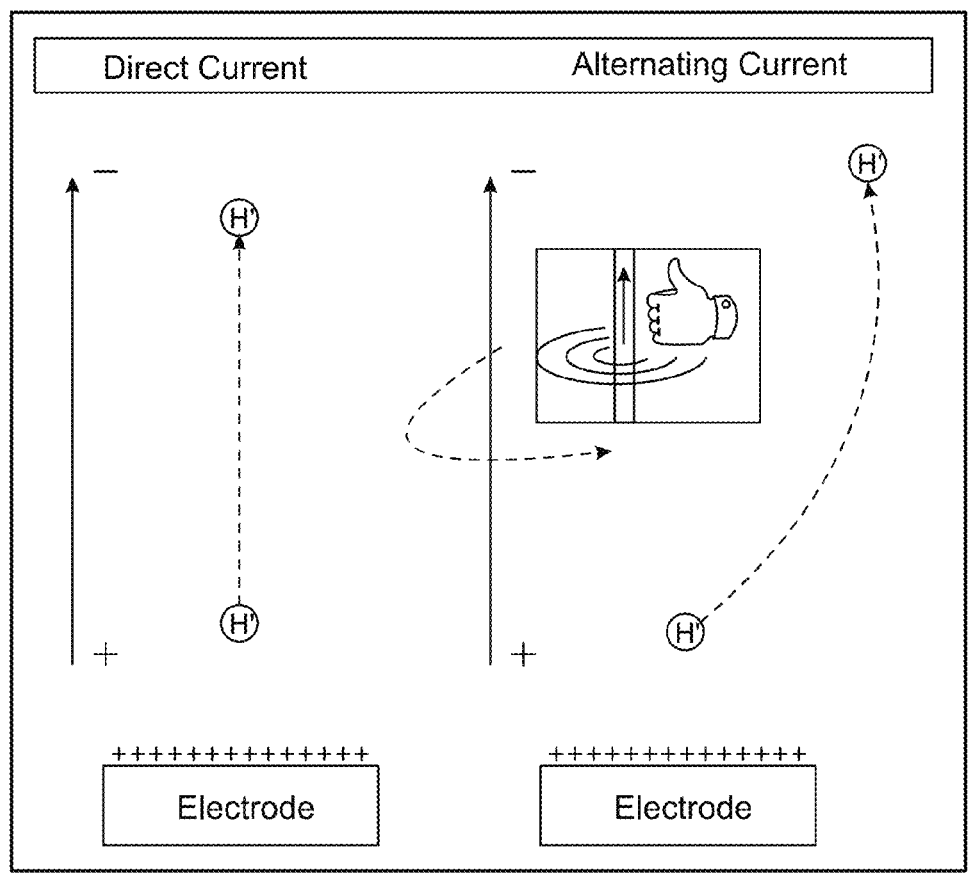
FIG. 11A-B illustrates Depiction of charged specie movement in a direct versus alternating current electric field.
Figure 11B:
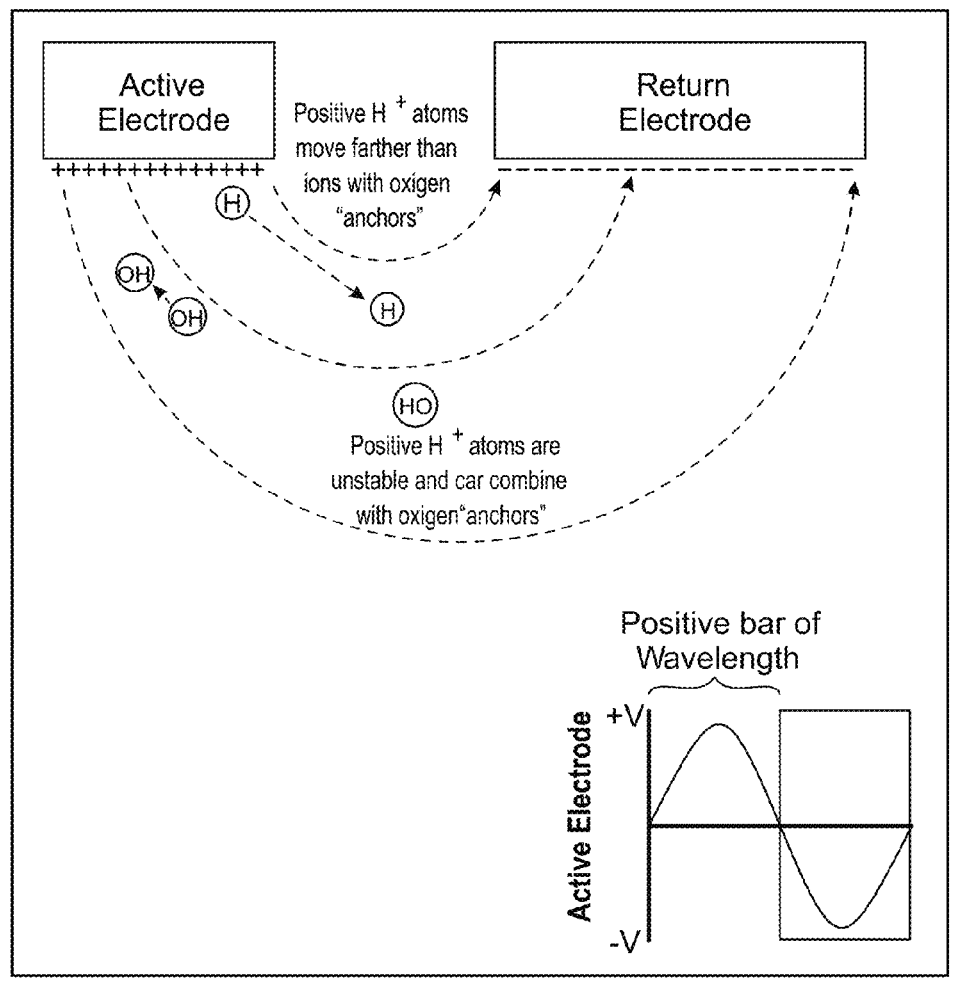

For example, sodium chloride solutions (300 mOsm/L) at 25° C. were treated with alternating current from 10 to 120 W with an 8500 V peak-to-peak setting (4250 peak voltage) and 390 kHz damped sinusoid bursts with a repetition frequency of 30 kHz into 500 ohms. This device configuration produces the redox reaction pair $$\alpha H_2O_{(l)} + \beta XCL \overset{energy}{\longleftrightarrow} (\alpha - \beta)H_{2(g)} + \qquad (14)$$

$$\frac{(\alpha - \beta)}{2}O_{2(g)} + \beta HCl_{(aq)} + \beta XOH_{(aq)}$$

$$(\gamma - \delta)H_{2(g)} + \frac{(\gamma - \delta)}{2}O_{2(g)} + \delta HCl_{(aq)} + \qquad (15)$$

$$\delta XOH_{(aq)} \overset{energy}{\longleftrightarrow} \gamma H_2O_{(l)} + \delta XCl_{(s)} + \Delta$$

with the variables α, β, γ, and δ as the molar quantities that satisfy the oxidation reduction valence requirements for the overall reaction set. Without reconciling reference frame transformations, when charged species move in electric and magnetic fields, the following two laws apply, the Lorentz force and Newton's second law of motion, which can be equated as follows:

$$F = Q(E + v \times B) \qquad (16)$$

$$F = ma = m\frac{dv}{dt} \qquad (17)$$

$$\left(\frac{m}{Q}\right)a = E + v \times B \qquad (18)$$

where F is the force applied, E is the electric field, B is the magnetic field, and v, m, a, Q are the velocity, mass, acceleration, and charge of the species, respectively. Referring now to FIG. 11A, depiction of charged specie movement in a direct versus alternating current electric field is illustrated. Alternating current magnetic fields cause curl forces in an orthogonal direction to the electric field similar to the right hand rule for circuits. Due to intermolecular bond dynamics of water, combined with device configuration, the magnetic component for the purposes of this engineering level relative scale analysis is reduced to condense the analysis to electric field influences. FIG. 11B, illustrates line art depicting proton build-up due to differential charged species movement depicting the positive half of the wavelength and free $H^+$ moving a much longer travel distance than $OH^-$ "anchored" by the heavier oxygen. At various travel distances, the $H^+$ form heavier species like $H_3O^+$, which are then anchored in place and won't return as far as the $H^+$ traveled outward as current polarity changes, resulting in a proton-based charge separation gradient.

Because the magnetic curl component is principally orthogonal to the electromotive force, it adds only a very small relative distance to the final travel from origin due to device configuration. By reducing this component through an engineering-level analysis, charged specie movement can be examined in a single dimension model by calculating charged species acceleration and distance traveled by equating as follows:

$$a = \frac{QE}{m} \qquad (19)$$

$$d = at^2 \qquad (20)$$

$$d = \frac{QE}{m}t^2 \qquad (21)$$

Accordingly, the relative travel distance between two different charged species, x and y, can be depicted as $$\frac{d_x}{d_y} = \frac{\frac{Q_x E t^2}{m_x}}{\frac{Q_y E t^2}{m_y}} \qquad (22)$$

During reactions (14) and (15) in sodium chloride solutions, the predominant reactant/product charged species present include $H^+$, $OH^-$, $Na^+$, $Cl^-$, and $H_3O^+$ for which relative scale travel distances are determined and correlated with electrochemical potential measures during irrigant formation. Because of widely fluctuating treatment venue conditions including numerous charge movement influences, the differential charged species separation resulting in electrochemical potential formation is modeled as proton travel distance, recruitment, and resultant pressure force as generated by a typical device system electric field of $3.1 \times 10^4$ V/m in order to provide benchmark solution parameters. [electric field model based upon average electrode separation of $$6.1 \times 10^{-3} \text{ m} \left[ \frac{1.74 \text{ mm} + 10.41 \text{ mm}}{2} \right].$$

$$\frac{V}{E(\text{m})} = \frac{(2000 \text{ V})\sin\frac{t}{2.6 \text{ }\mu s}}{6.1 \times 10^{-3} \text{ m}}$$

with average electric field of ½ alternating current period (1.3 μs at f=390 kHz and λ=2.6 μs) represented as $$E_{ave} = \frac{1}{1.3 \text{ }\mu s} \int_0^{1.3 \text{ }\mu s} \frac{2000 \text{ V}}{6.1 \times 10^{-3} \text{ m}} \sin\frac{t}{2.6 \text{ }\mu s} dt,$$

$$E_{ave} = \frac{2000 \text{ V}}{(1.3 \text{ }\mu s)6.1 \times 10^{-3} \text{ m}} \left( -\cos\frac{1.3 \text{ }\mu s}{2.6 \text{ }\mu s} - -\cos\frac{0}{2.6 \text{ }\mu s} \right) \mu s,$$

and $$E_{ave} = \frac{2000 \text{ V}}{7.93 \times 10^{-3} \text{ }\mu s * \text{m}} (-.0878 + 1) \mu s = 3.07 \times 10^4 \text{ V/m}.$$

[Note that this estimation accepts a tenfold difference in the near and far distances between potential field lines]. (See FIGS. 6-8).

Irrigant electrochemical potential versus power delivery is illustrated in FIG. 9 and relative travel distances between irrigant charged species are presented in Table 1. During energy delivery, an $H^+$ (proton) electrochemical potential gradient is created representative of charged specie separation and is directly correlated with power delivery. The charged specie relative travel distances indicate that differential proton movement is highest based upon charge/mass ratios. The resultant charge separation functions as a redox magnetohydrodynamic proton pump that can be delivered to tissue surfaces through charge carriers.

From equation (8), proton travel distance in a vacuum under irrigant creating forces is $$d_H+(\text{m}) = \frac{(1.6 \times 10^{19} C)\left(3.1 \times 10^4 \frac{V}{m}\right)}{1.67 \times 10^{-27} \text{ kg}} (1.3 \times 10^{-6} S)^2 \quad (23)$$

which yields the result of $d_{H^+}$=5.02 m. Result obtained by substituting $$\left[ 1 \text{ V} = 1 \frac{(N)(m)}{c} \right]$$

with $$\left[ 1 \text{ N} = 1 \frac{(kg)(m)}{s^2} \right]$$

to yield $$\left[ 1 \text{ V} = 1 \frac{(kg)(m^2)}{(C)(s^2)} \right].$$

By multiplying the average electric field $3.1 \times 10^4$ V/m by the average electrode separation $6.1 \times 10^{-3}$ m, the average voltage 189.1 V is determined and can be used to obtain current at a specified power setting. For 25 W, $$P = VI \quad (24)$$

$$I = \frac{25 \text{ W}}{189.1 \text{ V}} = 0.132a = 0.132\frac{C}{s} \quad (25)$$

Within the 1.3 μs alternating current half period, the irrigant creating current generates charged species as depicted by $$0.132\frac{C}{s}(1.3 \times 10^{-6} s) = 1.7 \times 10^{-7} C \quad (26)$$

$$\text{\# of Carriers} = 1.7 \times 10^{-7} C \div \frac{1.6 \times 10^{-19} C}{\text{\#ofChargeCarriers}} = 1.1 \times 10^{12} \quad (27)$$

Assuming the carriers will be represented evenly between positive charges (such as $H^+$) and negative charges (such as $OH^-$) and that 99.1% of charge is split water, $5.4 \times 10^{11}$ charge carriers in solution produce approximately $5.3 \times 10^{11}$ protons that move during the positive portion of the alternating current signal.

Because of the intermolecular hydrogen bond flicker rate of water, the force of each proton can be modeled from equation (3) whereby $$F = QE \quad (28)$$

$$F_{H^+} = (1.6 \times 10^{-19} C)\left(3.1 \times 10^4 \frac{kgm^2}{mCs^2}\right) = 5.0 \times 10^{-15} \text{ N} \quad (29)$$

$$\sum F_{H^+} = (5.3 \times 10^{11} H^+ \text{ions})(5.0 \times 10^{-15} \text{ N}) = 2.7 \times 10^{-3} \text{ N} \quad (30)$$

In creating a designed irrigant for therapeutic application, a device plenum area opening of 7.2 mm² ($7.2 \times 10^{-6}$ m²) generates a proton pressure which can be represented as $$P_{H^+} = 2.7 \times 10^{-3} \text{ N}/(7.2 \times 10^{-6} \text{ m}^2) \approx \quad (31)$$

$$370 \frac{\text{N}}{\text{m}^2} \approx 0.05 \text{ psi}\left(\frac{lb_f}{in^2}\right) \approx 2.8 \text{ mmHg}$$

Figure 6:
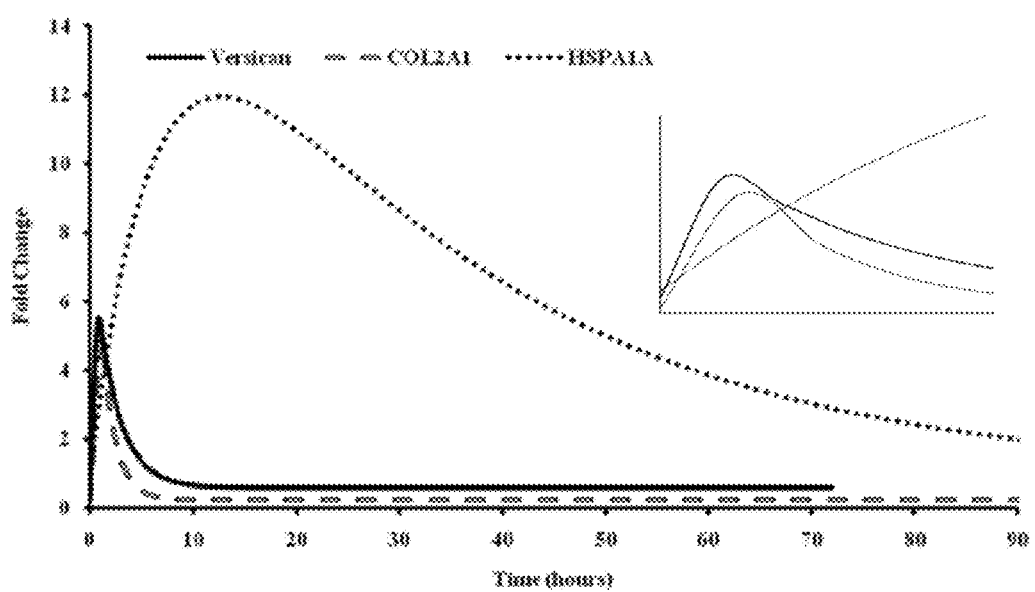
FIG. 6 illustrates curve fit regression depicting transcriptional up-regulation in subadjacent surface chondrocyte after non-ablation radiofrequency lesion stabilization.
Figure 7A:
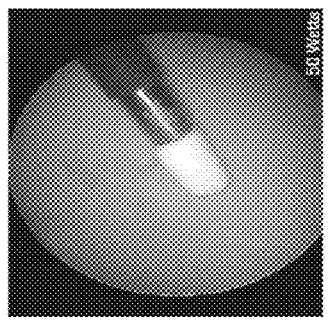
Figure 7B:
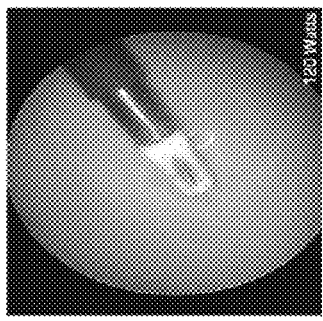
Figure 7C:
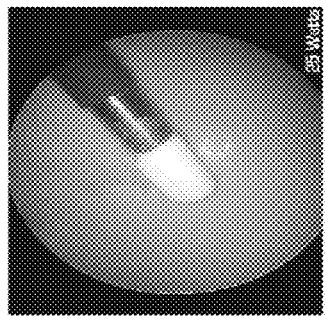
Figure 7D:
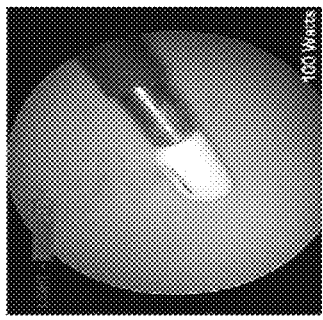
Figure 7F:
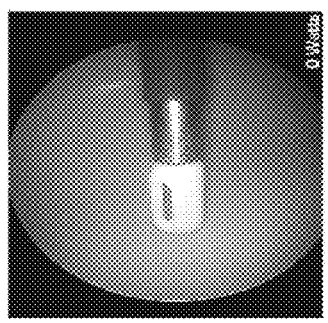
Figure 7F:
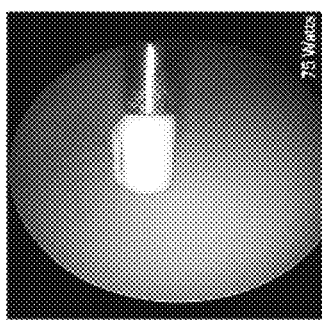

Electromagnetism influences the interactions between electrically charged species thereby governing chemical processes. Although the time and spatial responses of charges are complex, understanding the constituents of a particular venue can allow charge separation modeling (FIG. 6). In creating irrigants designed for the targeted tissue, attendant non-ionizing electromagnetic field quanta cause a distortion of alternating current circuit reaction dynamics in saline solutions consistent with water's cooperative hydrogen bonding. Because intermolecular hydrogen bond stretching frequencies of water demonstrate a proton based femto- to pico-second oscillation period, electron movements associated with alternating current polarity changes are less rapid so that water protons experience direct current forces ($10^{12-15}$ Hz flicker rate versus $10^{5-6}$ Hz circuit frequencies). Accordingly, this high proton mobility and intermolecular dynamics of water allows modeling as a single dimensional direct current circuit to determine relative scales that are pertinent for biologic applications.

Figure 12:
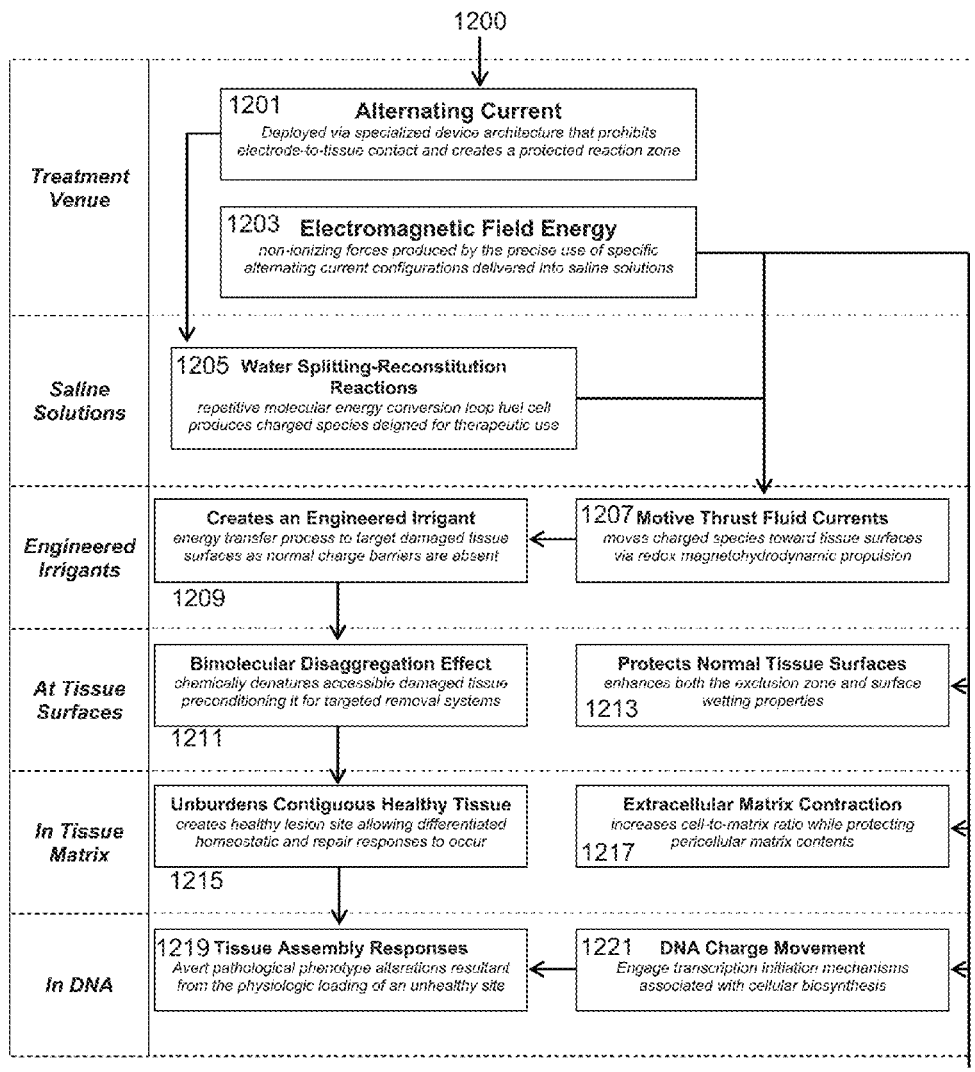
FIG. 12: Tissue rescue algorithm according to one embodiment is illustrated.

Device constrained redox magnetohydrodynamic forces induced by alternating current circuits in saline solutions produce motive delivery gradients that transport protons in much the same manner as that of biologic proton pump mechanisms resulting from electron transport chains. The modeled pressure forces of the irrigant proton gradient are similar in magnitude to the transcapillary net filtration gradient required to generate normal net capillary filtration. Further consideration to the many influences on specific charged species in saline solutions and other attractive-repulsive forces present during treatment are required to detail the therapeutic deployment of irrigants engineered for electrochemical potentials. These processes produce charge separations based upon charge-to-mass ratio profiles with biologically appropriate motive forces. These same mechanisms have been applied to the understanding of other biologic processes that occur during therapeutic intervention. Based upon the foregoing, FIG. 12 depicts a tissue rescue algorithm for the methods and devices described herein. Referring now to FIG. 12, a tissue rescue energy-based device as described herein 1200 according to one embodiment of patent invention, provides for early surgical intervention designed to mitigate the disease burden of tissue surface-based medical conditions through safe lesion stabilization. Alternating current 1201 at the treatment venue is deployed via specialized device architecture that prohibits electrode-to-tissue contact and creates a protected reaction zone. Electromagnetic field energy 1203 are non-ionizing forces produced by precise use of specific alternating current configuration delivered into saline solutions. Water splitting reconstitution reactions 1205 of saline solutions provide repetitive molecular energy conversion loop fuel cell activity and produces charged species designed for therapeutic use. Motive thrust fluid currents 1207 move charged species toward tissue surfaces via redox magnetohydrodynamic propulsion. An energy transfer process 1209 creates an irrigant engineered to target damaged tissue surfaces as normal charge barriers are absent. The normal tissue surface is protected 1213 and the exclusion zone and surface wetting properties are enhanced. Irrigants engineered 1209 are directed to tissue target surface 1211 and chemically denatures accessible damaged tissue preconditioning the targeted tissue for removal.

At the tissue matrix level, irrigant engineered as described in 1209, unburdens contiguous healthy tissue and creates healthy lesion site allowing differentiated homeostatic and repair responses to occur 1215. An electromagnetic field energy 1203 induces an extra cellular matrix contraction increases cell to matrix ration protecting pericellular matrix 1217 and increases cell-to-matrix ratio while protecting pericellular matrix contents. At the genomic level, an electromagnetic field energy 1203 as described engages transcription initiation mechanisms associated with cellular biosynthesis 1221. Irrigants engineered as described in 1209 induce tissue assembly responses 1219 averting pathological phenotype alterations resultant from the physiologic loading of an unhealthy site.

Even though the consequences of over-resection for tissue-surface based medical conditions include disease progression, early morphologic surface changes remain an attractive therapeutic target as this setting retains the elements in situ for normal homeostasis and repair. Because of the resection precision required (μm-nm scale) and since tissue surfaces reside within a saline milieu, maintaining cell viability and a differentiated phenotype around a lesion site stabilized relative to its perturbation specificity and modality requires knowledge of saline-to-tissue interfaces during disease-related changes in tissue boundary structure-function.

Accordingly, the mechanisms by which organisms construct and utilize saline charge barriers provide a therapeutic substrate at the requisite scale from which interventions can be devised that do not injure this barrier at normal tissue surfaces yet take advantage of its disruption at diseased tissue sites. This scale-appropriate trait-targeting challenge has been met by IMRB generated and deployed irrigants that physiochemically loads tissue surfaces in an irrigant manner based upon germ layer independent but charge dependent mechanisms. Treatment with a "physiochemical scalpel" are methods according to one embodiment of the present invention designed to accelerate lesion recovery by inducing advantageous cell-to-matrix modifications and stimulating differentiated tissue assembly repair functions within the retained contiguous tissue utilizing irrigants engineered with proton availability from an IMRB.

When charges in fluid media are manipulated with energy, products include useful molecules such as irrigants (referred to as irrigants because of the fluid milieu as well as the manner in which the products are delivered to tissues) that are created purposefully to bathe targeted tissue sites as a means to induce tissue changes specific for preconditioning or manipulating tissue characteristics. The irrigant bath includes charge accelerations, for example, hydrogen ion (proton) delivery within the irrigant that treats tissues—like an acid shift in the irrigant. When this charge is purposefully induced within tissues, the products may also include electromagnetic forces that affect tissues at and below the surface level, unencumbered tissues (tissues subsequent to therapeutic intervention due to removed diseased tissue without collateral damage to healthy tissue). These forces alter gene expression by mechanisms such as electron acceleration within macromolecular tissue constituents including DNA. The induced electromagnetic fields create repulsive forces within molecular assemblies such as double strand or triple strand polymers. The electron acceleration can cause strand separation, which in the case of DNA initiates transcription at specific promoter domains.

The manipulation of charges as explained more fully herein in either local, tissue surface or subsurface, is the charge/mass ratio, and for electrons manipulated by radiofrequency energy, this process utilizes a high charge/mass ratio. The high charge/mass ratio is useful for manipulation of a fluid media, for example saline. The products delivered to the tissue include a shift towards acid production, which is another way of describing hydrogen ion or proton delivery to tissue surfaces dependent upon the acceleration of those electrons. Protons can be carried in the media via various compounds like sodium hypochlorite. Further, a high charge/mass ratio is useful within tissues because it does not damage normal tissue but instead stimulates specific responses such as a charge acceleration creating an electromagnetic field having a threshold slightly above microenvironmental perturbation noise for example molecular vibrations that occur naturally within the tissue structures that we treat. A small field guards against iatrogenic injury within retained contiguous tissue. Further, ion exchanges are an important process at tissue interfaces because of the charge accelerations that are occurring. These exchanges are induced in tissue surface barriers, like boundary lubrication mechanisms, based upon the element (i.e. $H_2O$, $Na^+Cl^-$) makeup of the irrigant fluid into which the energy is deployed.

For example, manipulation of the phospholipid layer, the surfactant layer, is an important mechanism to protect tissues during irrigant delivery. Cation exchanges are utilized by altering the monovalent and divalent cation concentration of the interfacing media. Cation ion exchanges change the properties of tissue surface barriers to either protect them or to alter their properties to benefit treatment.

Proton delivery to tissue surfaces exposed to or within a fluid media environment may be driven by radiofrequency acceleration of electrons that retain high charge/mass ratio. A high charge/mass ratio is needed so that the energy requirements to drive the acceleration of electrons is low to avoid or minimize iatrogenic injury from excessive energy input to the body. These low energy requirements drive the created protons to tissue surfaces that interact with diseased biologic tissue but are not disruptive to normal tissue surfaces. A device as described in U.S. Pat. Nos. 6,902,564, 7,066,932, 7,819,864, 7,713,269, 7,445,619, 7,771,422, 7,819,861 or 7,354,438 for example having an electrosurgical plenum facilitates this low energy deployment.

Electron acceleration within tissues is needed because of this high charge/mass ratio and low energy requirements. Initiating gene expression with energy that is not injury inducing to the tissue promotes healing of the treated tissue. The initial tissue assembly or repair responses of cells are characteristically governed by low threshold excitation relative to ambient E-M fields and show responsiveness just above environmental perturbation—this is because of the nature of tissue homeostasis, that cells need to respond quickly to changes in their environment. Electromagnetic fields deployed herein accomplish this because of the high charge/mass ratio utilizing electrons at a level that does not cause tissue damage at the subsurface, but utilize normal homeostatic and repair mechanisms.

Systems and methods as described herein can be utilized for any tissue surface based lesions, for example articular cartilage. The effects are delivered in situ at the lesion site, rather than an external delivery like other electromagnetic field producing devices. In one embodiment of the present invention, the intimate relationships between tissue surface barriers and their saline environments create a therapeutic substrate for the surgical rescue of diseased tissue.

One embodiment of the present invention provides for early intervention by enabling the therapeutic enrollment of contiguous tissue healing phenotypes that make lesion reversibility possible. For example, osteoarthritis results in whole joint-organ disease persuaded by articular cartilage integrity failure. Because damaged cartilage serves as a biologic-mechanical irritant that causes symptoms and advances disease, treatment efforts designed for its removal remain an intuitive and important focus intended to maintain articular cartilage integrity and alleviate disease burden. Yet, lesion stabilization has been constrained by surgical interventions resulting in volumetric or functional over-resection that expand lesion size and provoke or advance disease progression. Despite past attempts to minimize over-resection, only recently has its elimination been enabled. Transformative discoveries of this magnitude are often initially plagued by doubts about their practical value; for osteoarthritis, these value assessments are additionally confounded by articular cartilage's reputation as a tissue type with a perceived poor healing capacity, even though this reputation may be largely due to the retention of damaged tissue artifacts that act as a biophysical irritant in the context of the historical inability to avoid scale-appropriate over-resection.

Articular cartilage is a highly differentiated and stratified tissue that retains a large portion of its adult healing phenotype at its surfaces. Because cartilage lesions can progress slowly, reflecting retained contiguous differentiated homeostatic resistance capacity against the degree to which diseased tissue burden becomes overwhelming, eliminating over-resection is often viewed as a tissue rescue designed to unencumber contiguous tissue function and minimize downstream morbidity. To preserve superficial healing properties heretofore fully eliminated as collateral damage, surgical resection requires "vim level" precision; further, normal tissue surface barrier regimes are structured at the "nm level", presenting a challenging venue to guard against iatrogenic injury. Consequently, surgical precision necessitates a unique "physiochemical scalpel" approach that includes replacing traditional surgical visual-tactile cues with treatment endpoints borrowed from comparative explant microhistology. Although treatment endpoint cue evolution can influence new technology adoption rates, cartilage management education toward a cognitive map is being encouraged by socioeconomic pressures supportive of over-resection as unnecessary, harmful, and liability-laden. As it is difficult to imagine informed patients forgoing the opportunity to preserve their tissue longer, either by replacing cartilage lesions with larger ones or simply waiting for diseased tissue to overwhelm contiguous differentiated homeostatic resistance capacity, the rapidly emergent obsolescence of over-resection also reflects consumer pressures.

The benefits of tissue rescue to unencumber contiguous tissue function are considerable. Prior to surmounting the over-resection treatment barrier that enabled tissue rescue, lesion reversibility was clinically inaccessible. Since contiguous differentiated homeostatic resistance capacity can give way to the burden of damaged cartilage, tissue rescue seeks not only to unencumber contiguous tissue, but also to permit-enroll the tissues intrinsic homeostatic and repair capabilities to avoid irreversible phenotypic alteration or destruction. Uniquely, articular cartilage's superficial zone reveals molecular production specificity like clusterin, versican, and lubricin; chondrocyte migration in response to focal partial-thickness lesions; control of zonal reorganization; appositional growth; chondroproliferation; chondrocyte colony formation; and a side population source of mesenchymal progenitor cells that express stem cell markers, contractile actin isoforms, progenitor cell signaling mediators, and monolayer expansion behavior while maintaining a chondrogenic phenotype. Because articular chondrocytes display significant phenotypic plasticity and high anabolic capacity, improving their environment by targeted diseased tissue resection is an effective means to stabilize contiguous chondrogenic phenotype(s), even if that includes interrupting early phenotypic adaptations-alterations to disease.

As reversibility for some lesions may require a phenotypic shift (osteoarthritic chondrocyte redifferentiation) such as that induced by physiologic loading a healthier site, the capability to transiently upregulate focal chondrocyte biosynthetic activity reflective of differentiated tissue assembly repair mechanisms remains an important early post-treatment therapeutic desire.

Inducing in situ, targeted, appropriate, and differentiated biosynthetic cellular function within contiguous tissue subadjacent to diseased locales and thereby recruiting local chondrocytes to aid lesion recovery, requires the ability to access genomic control. These mechanisms that govern tissue assembly and display promoter domain-segment threshold responsiveness slightly above micro-environmental perturbation noise. As such, in vivo transcription initiation technology based upon charge/mass ratio dependent acceleration characterizes a revolution of function and enabled possibility for cartilage. Because of the enormous health gains to be realized by reducing osteoarthritis disease burden, the goal of unencumbered contiguous tissue and lesion reversibility becomes an effort difficult to ignore, despite cartilage lesion heterogeneity that may require nuanced device design.

Another example is directed to hyaline cartilage commonly encountered during arthroscopy for which the system and method of embodiments of the present invention may be applied. Early articular cartilage damage manifests as surface matrix changes such as that observed with the initial stages of osteoarthritis. Despite the heterogeneity of this damage, safe lesion stabilization (i.e. damaged tissue removal) is required to permit intrinsic homeostatic and repair responses since damaged tissue serves as a biologic and mechanical irritant impeding such responses and leading to symptoms and disease progression. Lesion stabilization for early articular cartilage disease constitutes a tissue rescue, allowing biologic tissue response properties to more fully manifest unencumbered rather than allowing the tissue to progressively convert to a mechanical adaptation construct characterized by further matrix failure. Because early intervention presupposes that tissue surrounding the lesion retains effective differentiated function, therefore chondrocyte viability and a healing phenotype are important attributes to retain within subadjacent tissue.

Thermal and plasma ablation technologies which deliver electrical current directly into tissue have been deemed inappropriate for articular cartilage tissue preservation procedures as a result of significant induced iatrogenic damage to subadjacent tissue associated with the high energy deployment necessitated by device design. Hyaline cartilage is a tissue type retaining a high water content ensuring that ablation technology will effectively pool electrothermal energies within cartilage tissue to a detrimental level. Ablation technologies cannot distinguish between normal and abnormal tissues because device design is not based upon tissue specific biology and consequently induce necrosis. This necrosis is caused for a variety of reasons, including the formation of subsurface tissue heat capacitance due to water permeability constraints at normal surfaces adjacent to lesions, the overwhelming metabolic disturbances of internal tissue electrolysis, and the surface entry wounds typical of electrical injury; all of which further impair tissue integrity and local biologic responses by expanding the size of the original lesion and further progressing disease. Non-ablation technology allows for the targeted removal of diseased tissue without expanding lesion size or compromising subsurface tissue with electrical current deposition.

Device architecture of one or more embodiment of the present invention ensures that the near-field reaction products are delivered only to tissue surfaces, not within tissues, and can selectively target damaged tissue, preparing it for mechanical débridement through inherent cleavage planes. Diseased articular cartilage is characterized by deteriorating surface-layered shear properties of collagen fibril disruption and orientation changes, weak collagen-to-proteoglycan bonds, proteoglycan depletion, aberrant water content, and decreased fixed charge density; this compromised tissue is further altered by the physiochemical loading delivered by non-ablation technology to a state amenable to gentle shear débridement during lesion stabilization. Shear stabilization in this instance illustrates treatment design relative to a tissue's perturbation failure specificity; understandably, safe lesion stabilization remains an advance inextricably necessary for disease burden mitigation.

The role of water at surgical treatment sites is an important factor to consider because of its ubiquitous presence in biologic assemblies. Tissue preserving surgical procedures can be difficult to create since they require balancing macroscopic treatment events with microscopic physiologic function. For example, many surgical treatment venues reside at tissue surfaces due to tissue integrity failures originating from surface forces or processes overloading tissue capacity to maintain integrity. Intact surfaces, whether articular cartilage, tendon, ligament or even other representative tissue types like gastric mucosa or lung pleura, are structured by water, often through variations in hydrophobic adhesion, to create a protective barrier designed to maintain tissue integrity against tissue-specific perturbations while maintaining lubrication zones that protect the underlying tissue matrix structure. Surface active phospholipid organization and absorption into lamellar superficial collagen layers constraining proteoglycan moieties is a common finding at the water-to-tissue interface that create the robust physiochemical charge barrier of tribiologic systems. These surface active phospholipid layers are often amorphous (without collagen), non-fibrous, or gel-like and can reconstitute via self-assembly after removal. These can reconstitute even after removal deep to collagen layers, through polymorphic aggregation forces like the hydrophobic effect governed by water. It is interesting to note that many anatomic tissue surface sites subjected to repetitive perturbation have similar tissue homeostatic and repair mechanisms. These mechanisms allow for collagen based layered or cleavage plane failure as a back-up mechanism to topographic loss of water-structured amorphous surface barrier regimes that can occur during physiologic loading. This surface-based collagen cleavage plane failure is generally a reversible lesion under certain circumstances, most notably with damaged tissue removal while maintaining cell viability and differentiated phenotype around a lesion site stabilized relative to perturbation specificity.

Non-ablation technology exploits this common tissue surface characteristic for tissue preserving lesion stabilization by augmenting those structural planes during selective preconditioning or modification of diseased tissue that has become accessible due to the loss of the surface regime barriers. It is further interesting to note that these normal tissue surface regimes are rather robust because of water's structural interfacial organization, such that the reaction products originating from the electrosurgical plenum at tissue preservation settings cannot disrupt this barrier. Hence, undamaged surface tissue is protected. Indeed, disruption requires prolonged perturbations like enzymatic incubation, strong detergents, large single or cumulative insults, or even ablation energies. Additionally important is that the healthy bed of lesions being stabilized is also a barrier to such treatment due to the integrity of those same tissue constituents which when diseased are susceptible to tissue specific non-ablation physiochemical loading regimens.

Tissue edema, or an increase in tissue water content distinct from tissue surface water, is often an early event associated with injury or disease occurring prior to observable morphological changes. The increased water content can be due to either an alteration in tissue constituent structure or the re-localization of additional tissue components. Surgical targeting of tissue with an increased water content but without observable macroscopic alterations remains difficult. It is for this reason that most surgical device development is based upon observable criteria that the surgeon can readily identify during the procedure. Surface-based morphologic changes are uniquely suited as a therapeutic target, particularly since early intervention in these settings is governed by the ability to pursue tissue rescue as a result of creating an environment amenable at least to homeostasis and at best to self-repair.

The use of an electrosurgical plenum serves many functions, one being primary reaction zone manipulation within its interior. Configuration changes in its architecture can alter the formation and delivery of reaction products during targeted physiochemical loading of tissue surfaces. Two reaction products, pH and temperature, were evaluated because they are especially relevant to the function of water at tissue surfaces during physiochemical loading in a sodium chloride milieu, even though many other associated physiochemical phenomena are simultaneously occurring and warrant description.

For instance, a purposeful change in pH can be configured toward a strict linear regression by further shielding the primary reaction zone from the fluid-flow and convective forces at the treatment site. The temperature at the tissue or the media that interfaces with the issue can be manipulated. For example, heat can be delivered to tissue surfaces by creating localized temperature changes in the interfacing media rather than within the tissue itself as occurs with ablation technologies. Water has a high specific heat capacity and heat of vaporization therefore, it buffers heat delivery in a protective manner. Purposeful modulation of reaction product that escapes from the primary reaction zone coupled with a surgical intervention that is dependent upon positioning of an electrosurgical plenum of a electrosurgical device as previously described in U.S. Pat. No. 7,819,861 is a useful process to control the character such as duty-cycle, pH shift, ion-specific delivery and the like of treatment-specific reaction product that is delivered to tissue surfaces during physiochemical loading.

In one embodiment of the present invention, temperature change as a function of initial interfacing media temperature has been designed to protect tissue surfaces from inadvertent temperatures that may have an undesirable efficacy. While tissue surfaces, like phospholipid layers, can be sensitive to temperature changes, a device as employed in one experiment was designed to induce only a small temperature change of the interfacing media with a protective triphasic behavior. Further tissue preserving settings may be employed within Phase 1 (for example, low energy phase typically below 35 W with no significant oxidation/reduction gas generation during which no temperature change is deployed).

In addition to the protective role that ambient water serves during non-ablation treatment of legions as described herein, it also serves a protective role at tissue surfaces because the water is absorbed and held by tissue surface constituents. These tissue surfaces are robust due to water's influence on their constituents' polar regions with positively charged ends anchored to the negative charge density of proteoglycan typical in collagen constrained extracellular matrix. For example, hydration shells around phospholipids bind water via hydrogen and electrostatic bonds and when combined with hydrated ions become effective lubricants between sliding charged surfaces. This composition creates a strong laterally bonded network that is protective against shear forces by exhibiting lipid mobility and viscous resistance.

For physical load bearing tissue, the surface amorphous layer can support the majority of a load within its water phase thereby altering the liquid-solid phase load sharing of subsurface tissue by protecting the solid phases from elevated stresses. This water-to-tissue interfacial phenomenon is important in boundary lubrication regimes; and, it is the loss of this layer that facilitates further matrix failure leading to collagen based tissue damage. Should damage to the collagen progress without effective repair, it will serve as a lesion site irritant impeding natural reconstitution of the amorphous boundary lubrication layer and lead to further tissue overload matrix failure through additional loading of a damaged and poorly structured biomechanical site. Because this layer has been noted to reform after perturbation removal, its reconstitution, along with the favorable biomechanical environment of damaged tissue removal that stimulates more appropriate mechanotransductive biosynthetic gene expression, validates the approach of early intervention designed as a tissue rescue by removing an irritant and allowing cellular and matrix component repair to manifest relative to perturbation specificity.

According to one embodiment of the present invention tissue water is a therapeutic target for electromagnetic force. Non-ablation tissue treatment allows therapeutic regimens to be formulated at tissue surface and subsurface levels independently, but which may nonetheless be interrelated. Physiochemical loading of tissue surfaces as a treatment platform is a complex discipline because it requires an understanding of tissue biology in both the native and diseased state. Various physiochemical loading regimens can be created based upon tissue-specific therapeutic goals by modification, according to one or more methods described herein, of the reactants and products available in the primary reaction zone. Because the physiochemical loading of tissue surfaces is geographically or anatomically decoupled from subsurface tissue, non-ionizing electromagnetic forces at and below tissue surfaces are enabled and particularly useful for an early intervention strategy since subsurface tissue in this setting demonstrates retained cellular viability and a differentiated functional phenotype. Electromagnetic fields facilitate charge flow through accelerated transfer rates and changing valence configurations and have been associated with increased enzymatic reaction efficiency, DNA stimulated biosynthesis, superficial extracellular matrix volume contraction, cellular cytoprotection, and other domain specific gene expression modulation.

In biologic tissue, water remains a substrate for non-ionizing electromagnetic forces. The water acts as a facilitator of charge transfer because of its mobility around hydrogen bonds. However, the mechanisms by which electron transfer (often associated with redox chemistry) interacts with proton transfer (often associated with acid-base phenomena) in the presence of charged macromolecular tissue constituents that depend upon water to organize tertiary and quaternary structure and bond interactions are not fully defined. Therefore, non-ionizing electromagnetic field induced changes in biologic tissue requires in most instances further characterization of a tissue's specific elements within the native and diseased state available for targeted manipulation.

Safe stabilization of articular cartilage lesion is an important early surgical intervention advance toward mitigating articular cartilage disease burden. According to a system and method of an embodiment of the present invention, short-term chondrocyte viability and chondrosupportive matrix modification have been demonstrated within tissue contiguous to targeted removal of damaged articular cartilage. Surface chondrocyte responses within contiguous tissue after lesion stabilization according to an embodiment of the present invention is described. Non-ablation radiofrequency lesion stabilization of human cartilage explants obtained during knee replacement was performed for surface fibrillation. Time-dependent chondrocyte viability, nuclear morphology and cell distribution, and the temporal response kinetics of matrix and chaperone gene transcription indicative of differentiated chondrocyte function were evaluated in samples at intervals to 96 hours post-treatment. Subadjacent surface articular cartilage chondrocytes demonstrated continued viability for 96 hours post-treatment, a lack of increased nuclear fragmentation or condensation, persistent nucleic acid production during incubation reflecting cellular assembly behavior, and a transcriptional up-regulation of matrix and chaperone genes indicative of retained biosynthetic differentiated cell function. This outcome provides evidence of treatment efficacy and suggest that the application of the non-ionizing electromagnetic forces impact cellular function to promote recruiting local chondrocytes to aid lesion recovery.

According to one embodiment of the present invention, non-ablation treatment of diseased tissue enables targeting of diseased tissue by utilizing a protected electrode architecture for example the architecture described in U.S. Pat. Nos. 7,445,619 and 7,771,422. The device tips inhibits electrode-to-tissue contact so that the resistive tissue heating and tissue electrolysis induced by current delivery into tissue and associated with tissue necrosis do not occur like in thermal and plasma radiofrequency ablation devices. The protective housing creates a primary reaction zone that is shielded from the large physical fluid-flow and convective forces present during surgical application enabling deployment of low-level radiofrequency energy delivery into interfacing media rather than into tissue to create physiochemical conversions that can be used for surgical work.

By manipulating active electrode current density dispersion, a repetitive molecular energy conversion loop under non-ionizing electromagnetic forces is created wherein the rapid splitting and reconstitution of the water molecule occurs. Similar to the technology utilized in a fuel cell that harnesses energy from the molecular bonds of water, these physiochemical conversions create products that are concentrated through techniques such as capacitive deionization and concentration enrichment and delivered to tissue surfaces through selective throttling by the protective housing in a controlled and localized fashion through precipitation, sedimentation, thermal, or chemical gradient forces via redox magnetohydrodynamic fluid flow.

Diseased tissue is preferentially more sensitive to this physiochemical loading as compared to non-diseased tissue, allowing for selective modification and preconditioning toward a state amenable to safe and effective gentle mechanical débridement with the edge of the protective housing through augmented and naturally facile tissue cleavage planes inherent in articular cartilage. Non-ablation treatment of diseased tissue or tissue in need of treatment is a matrix-failure-based intervention that does not rely upon an electrode-to-tissue interface. The treatment physiochemically loads tissue surfaces in a manner that cannot be accomplished with the exposed electrodes of thermal and plasma radiofrequency ablation devices because of the induced internal cellular damage they create.

This physiochemical loading is uniquely suited to affect the accessible and degenerate surface matrix structure of damaged articular cartilage tissue preferentially rather than the intact chondron and matrix tissue deep to the surface lesion level. As an illustration, pH shifts can be generated, such as preferential sodium hypochlorite precipitation akin to production through neutrophil myeloperoxidase catalysis, and configured to react oxidatively with a wide variety of biomolecules at tissue surfaces including the exposed proteoglycan aggregates of damaged articular cartilage. Such pH shifts have been shown to produce mechanical alterations at articular cartilage surfaces through electro-chemo-mechanical coupling via site-specific hydrogen and disulfide bond alterations within constituent proteoglycan and collagen. These targeted pH gradients at tissue surfaces modulate mechanical and electrochemical tissue matrix properties by altering fixed and variable charge densities while affecting consequent extracellular intra-fibrillar hydration and osmotic character. This physiochemical loading of accessible surface-based diseased tissue can alter the relative ratio of tension-compression non-linearity toward a state amenable to gentle shear deformation mechanical débridement of tissue already characterized by the deteriorating surface-layered shear properties of collagen fibril disruption and orientation changes, weak collagen-to-proteoglycan bonds, proteoglycan depletion, aberrant water content, and decreased fixed charge density.

Optimizing the surface shear properties of early articular cartilage damage through cleavage plane stabilization is an important parameter for overall lesion stabilization relative to perturbation specificity. These mechanisms do not impair residual chondrocyte viability. These layered surface properties exploited for cleavage plane shear stabilization have been observed in other tissue types and locales requiring shear mitigation during surface degeneration and normally represent a back-up mechanism to boundary lubrication regime failures associated with perturbation exceeding homeostasis and tissue repair for reversible lesions.

It has been demonstrated previously that non-ablation technology selectively targets diseased tissue for removal without causing necrosis in contiguous healthy cartilage tissue while producing the chondrosupportive matrix modification of increased live chondron density in the Superficial Zone. Since chondrocyte viability in subadjacent tissue is not altered, the opportunity presents to evaluate chondrocyte behavior in response to lesion stabilization after treatment with one embodiment of the present invention. Notwithstanding the symptomatic improvement obtained from articular cartilage lesion stabilization, eliminating the mechanical and biologic joint burden, non-ablation technology begins to serve the larger disease burden represented by damaged articular cartilage.

The focal effects upon residual articular cartilage surface chondrocytes during lesion stabilization with non-ablation technology was experimentally examined by evaluating time-dependent chondrocyte viability, nuclear morphology and cell distribution, and the temporal response kinetics of matrix and chaperone gene transcription indicative of differentiated chondrocyte function.

Examples

As described herein, osteochondral specimens were harvested from patients undergoing total knee replacement under an approved Institutional Review Board protocol. The total knee replacement procedures were performed by a single surgeon in the normal course of his practice. The tissue to be normally discarded during the procedure was examined prior to harvest once the knee joint was entered surgically to determine if it met study inclusion requirements. Specimens were included that demonstrated an area of uniform partial thickness surface fibrillation of sufficient size from which matched-pair test samples could be obtained from each specimen. Specimens were divided into smaller test sample parts after harvest by sharp sectioning and were immediately transferred to an ex vivo saline arthroscopic treatment setting.

A non-ablation radiofrequency device designed for cartilage lesion stabilization was used per manufacturer's specifications (Ceruleau®; NuOrtho Surgical, Inc.; Fall River, Mass.). Lesion stabilization was performed by one surgeon accustomed to radiofrequency device use. The goal of the procedure was to remove the fibrillated cartilage damage and smooth the articular surface as determined by visual and tactile cues. Standard saline arthroscopic fluid was deployed at 20° C. with a fluid-flow rate of 30 cc/min±5 cc/min which created consistent fluid dynamics in the set-up typical of in vivo arthroscopy. Energy delivery (Valleylab Force FX™-C; Covidien, Inc.; Mansfield, Mass.) was standardized at 25 W with a 8500 V peak-to-peak setting (4250 peak voltage) and 390 kHz damped sinusoid bursts with a repetition frequency of 30 kHz into 500 ohms (i.e. COAG, fulgurate).

Lesion stabilization treatment time was 5 seconds for all specimens with a technique of moving the probe tip tangentially across the tissue surface with a consistent application pressure and speed as judged by the surgeon to mimic in vivo treatment conditions. The protective housing edge was used to gently shear-debride the fibrillated tissue concurrent with energy delivery for the allotted treatment time. Treatment did not deploy the heat delivery capabilities of non-ablation technology available through electrosurgical plenum positioning or increased energy levels that can be used for the more demanding lesion stabilization associated with less fibrillated tissue displaying a different degeneration-based collagen fibril-to-water structure. For treatment described herein the delivery of heat to tissue surfaces is limited by a triphasic nature to low temperature changes (i.e. $\Delta$0-7° C.) of interfacing media which is design-appropriate for the low thermal requirements that would be necessary to manipulate exposed surface type II collagen which begins to denature at 39° C. Paired sample explants served to generate untreated samples to serve as control that remained in an identical treatment bath during the procedure.

After treatment, the untreated and treated samples were randomly divided into three groups for evaluation of time-dependent chondrocyte viability, nuclear morphology and cell distribution, and the temporal kinetics of versican, COL2A1, and HSPA1A gene expression in surface chondrocytes.

The samples allocated to this group were evaluated at 1 hour and 96 hour intervals post-treatment for alterations in chondrocyte viability. Samples were prepared by thin sectioning to isolate the surface region containing Superficial and Transitional Zone chondrocytes and matrix from the remainder of the tissue (sample dimensions: 3 mm thick by 7 mm square). These surface cartilage specimens were left as bulk tissue and incubated at 37° C. in Dulbecco's Modified Eagle's Medium (Invitrogen, Inc.; Carlsbad, Calif.) with fetal bovine serum and 1% penicillin-streptomycin (10,000 units and 10,000 µg, respectively). No equilibration period was used and the specimens were incubated in 95% air with 5% $CO_2$. At 1 hour and 96 hours, three 0.5 mm coronal sections of each sample referencing the center of the untreated and treated sites were created and prepared for staining by washing in HEPES buffered saline solution. Live/Dead® Reduced Biohazard Cell Viability Kit #L-7013, (Invitrogen, Inc.; Carlsbad, Calif.) was used per manufacturer's specification to stain samples. Samples were gluteraldehyde fixed, transferred to standard flat glass slides, and flooded with VectaShield® fluorescence protection oil prior to the placement of #1.5 borosilicate glass cover slips over each sample section.

Confocal fluorescence laser microscopy analysis was performed by personnel blinded to the identity of the treatment groups for each sample. Confocal imaging was performed with an IX-81 inverted microscope coupled to a FV300 confocal laser scanning unit (Olympus, Inc.; Center Valley, Pa.) using continuous wave 488 nm laser excitation (Sapphire 488HP; Coherent, Inc.; Santa Clara, Calif.). Live cells were captured under the green fluoresce channel (505-525 nm) and dead cells were captured under the red fluoresce channel (577-634 nm), generating a Live image, a Dead image, and an Integrated image. Histologic characteristics and cell viability between untreated and treated samples were assessed by comparative image evaluation for change in live and dead cell populations.

The samples allocated to this group were evaluated at the 1 hour post-treatment interval to determine alterations in nuclear morphology and cell distribution. Samples were maintained after treatment in the arthroscopic saline bath and prepared by thin sectioning as above. Three 0.5 mm coronal sections of each sample referencing the center of the treatment site and control were created and prepared for staining by washing in HEPES buffered saline solution. Hoechst 33342 stain, trihydrochloride FluoroPure™ (#H-21492; Invitrogen, Inc.; Carlsbad, Calif.) was used per manufacturer's specification to stain samples. Samples were fixed and prepared for imaging as above.

Two-photon excitation microscopy was performed with an IX-81 inverted microscope coupled to a FV300 confocal laser scanning unit (Olympus, Inc.; Center Valley, Pa.) using a ×60, 1.2 NA water immersion objective (UPLSAPO 60XW; Olympus, Inc.; Center Valley, Pa.) for imaging. A dichroic mirror that reflected the near-infrared laser excitation light and transmitted the visible (~460 nm) bis-benzimide emission was used as the excitation dichroic. The excitation source was a mode-locked titanium sapphire laser (Broadband Mai Tai; Spectra Physics, Newport, Inc.; Irvine. Calif.) operating at 800 nm with a pulse width of ~100 fs and a pulse repetition rate of 80 MHz. An average power of ~30 mW (measured at the back aperture of the microscope objective) was used to excite the sample emission. A short pass filter with a cutoff wavelength of 680 nm (FF01-680/SP; Semrock, Inc.; Rochester, N.Y.) was used to filter residual 800 nm excitation laser light from the emission. Water was used as an immersion fluid to optically couple the sample and objective to the cover slip.

Serial x-y plane tomographic images along the z-axis were generated to evaluate nuclear morphology and cell distribution. Dye exclusion properties were not evaluated. These images were compressed into a single x-y image brining the nuclear contents along the z-axis image planes into a single composite view to facilitate additional inter-chondrocyte nuclear comparisons. BioView open source cross-platform application software (Center for Bio-Image Informatics, University of California; Santa Barbara, Calif.) was used to evaluate cell distribution patterns since all sample chondrocyte nuclei stain with bis-benzimide. Axis rotations were performed to evaluate matrix modifications of treated versus untreated samples that may affect cell distribution patterns as noted previously.

The samples allocated to this group were prepared by thin sectioning (sample dimensions: 2 mm thick by 5 mm square) and incubated as above. Untreated and treated samples were randomly assigned to incubation intervals of 1, 24, 48, 72, and 96 hours. At the end of each incubation interval, the samples were frozen in liquid nitrogen and stored at −80° C. prior to RT-PCR testing. At testing, the samples were thawed and mechanically homogenized in lysis reagent (QIAzol

79306; Qiagen, Inc.; Valencia, Calif.). The homogenate was separated into aqueous and organic phases by centrifugation; and, mRNA was subsequently isolated by spin column elution (RNeasy Lipid Tissue Mini Kit #74804; Qiagen, Inc.; Valencia, Calif.).

Quantitative reverse transcriptase RT-PCR was performed (7300 Real-Time PCR System; Applied Biosystems, Inc.; Carlsbad, Calif.) by monitoring the increase in reporter fluorescence of Taqman® gene expression assays (Applied Biosystems, Inc.; Carlsbad, Calif.) for versican (#Hs00171642_m1), COL2A1 (#Hs00264051_m1), and HSPA1A (#Hs00359163_s1). RNA concentration obtained was determined for both untreated and treated samples and evaluated for significant differences; sample purity was evaluated for each specimen by determining $R_{260/280}$ values (ultraviolet absorbance ratio at 260 nm and 280 nm). Expression changes were quantified by the comparative $C_T$ method to calculate relative fold changes normalized against 18s rRNA, calculated as the difference ($\Delta C_T$) between the $C_T$ value of the target and 18s rRNA control. Each sample was assayed in duplicate with relative expression calculated and tabulated as $2^{-\Delta\Delta C_T}$ relative to each incubation interval sample group. The mean and standard deviation were calculated for each fold change grouping. Curve fit regression analysis for mRNA expression temporal kinetic fold change was performed (TableCurve 2D, version 5.01.02; Systat Software, Inc.; Chicago, Ill.) for the treated sample groups compared to the average $\Delta C_T$ of the 1 hour untreated sample group serving as control and as time zero designed to demonstrate the relative scale of expression responses over time.

Four samples were allocated to this group; two untreated and two treated. The untreated samples demonstrated surface fibrillation consistent with gross visual inspection of the tissue at the time of harvest. The Superficial Zone was disrupted by the fibrillation, but chondron appearance typical of this zone remained present in and around the fibrillation. Live cells were abundantly observed with only occasional dead cells residing in extruded positions at the frayed margins of the fibrillated tissue. Treated samples displayed elimination of the fibrillated tissue and smooth surfaces at the treatment site. No evidence of necrotic tissue was present with the surfaces subadjacent to the removed damaged tissue retaining Superficial Zone characteristics typical of the intact Superficial Zone regions of the untreated samples. An increase in dead cell populations was not evident in either the 1 hour or the 96 hour treated samples over the untreated sample groups; nor was a decrease in chondrocyte viability observed relative to incubation time. FIG. 1 depicts a representative post-treatment integrated Live/Dead cell viability stain section image demonstrating surface characteristics and viable chondrocytes without evidence of necrosis or altered cellular viability. Note the lack of dead chondrocytes and a smooth surface in the tissue subadjacent to the targeted removal of surface fibrillated tissue damage. Original magnification 10×.

Figure 2:
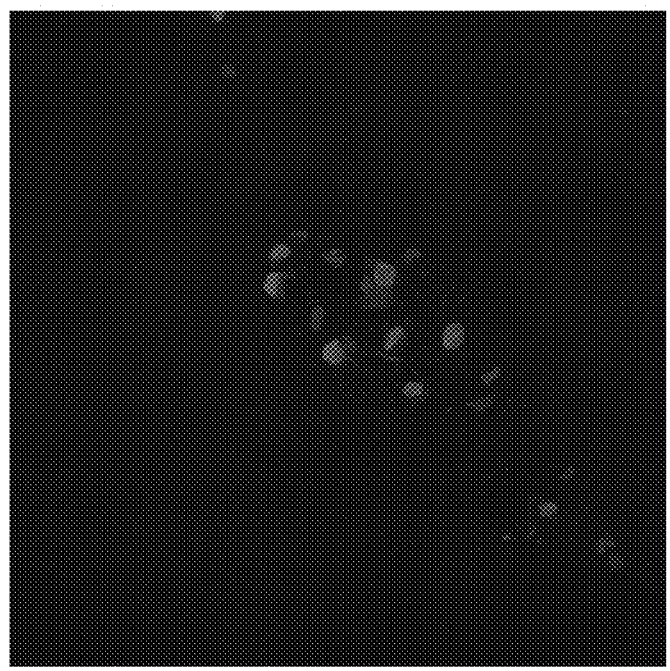
FIG. 2 illustrates a representative two photon confocal composite image of Hoechst stained chondrocytes with the tomographic z-axis images compressed into a single image.
Figure 3A:
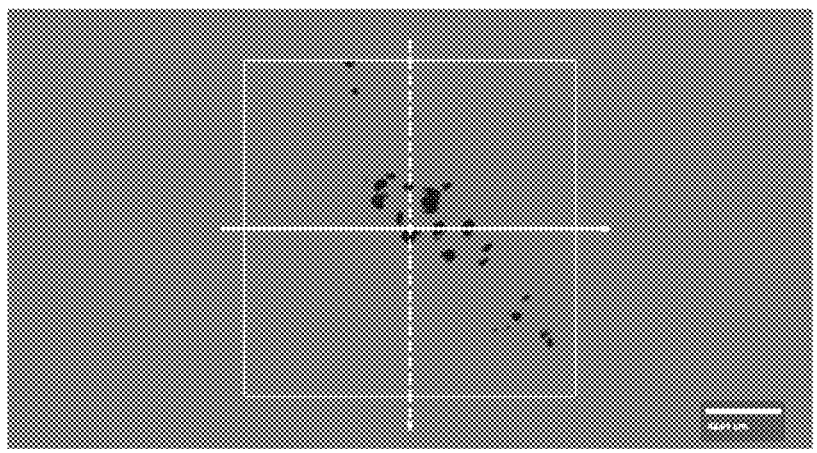
FIG. 3A-C illustrates a representative BioView images used to assess three dimensional chondrocyte distribution patterns.
Figure 3B:
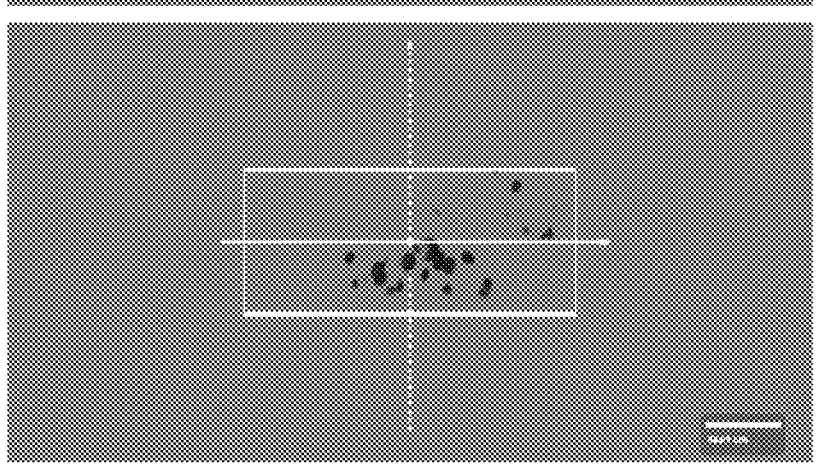
Figure 3C:
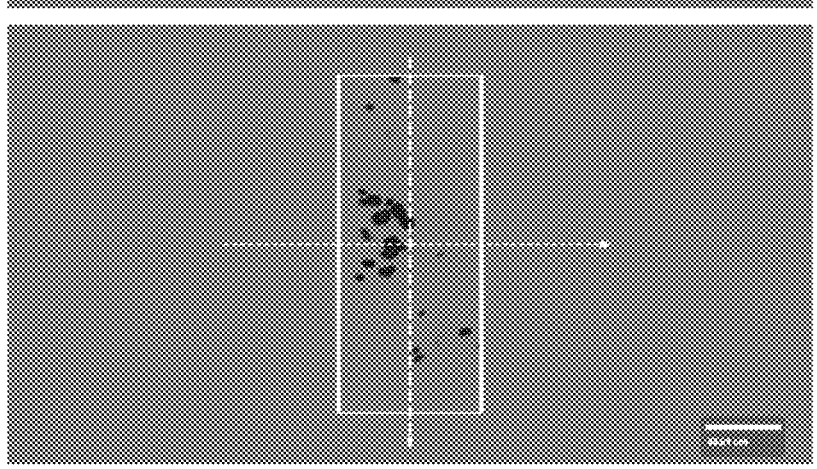

Four samples were allocated to this group; two untreated and two treated. The serial tomographic images demonstrated no evidence of altered nuclear morphology when compared to untreated samples. As depicted in FIG. 2, nuclear fragmentation or condensation (i.e. peripheral segregation or aggregation of chromatin into dense areas along the nuclear membrane) were not present within the tissue chondrocytes subadjacent to the tissue targeted for removal, reflecting no evidence of chondrocyte apoptosis. Note the similar staining intensities and lack of nuclear fragmentation or condensation. [Original magnification 60× water.] Cells typically contained a large nucleus with loosely packed euchromatin and little more dense heterochromatin. Homogeneous staining intensities appeared uniform in the z-axis compressed images. Occasional single randomly positioned cells demonstrated altered nuclear morphologies in some samples which could not be linked to the treatment site and likely represented fixation-dependent or other causes typical within articular cartilage. FIG. 3A-C depicts a representative BioView images of cell distribution viewed from the x-y, x-z, and y-z vantage points. FIG. 3 (A) depicts the x-y plot; (B), the x-z plot; and (C), the y-z plot. Solid, dotted, and dashed lines with arrows reflect coordinate orientation between the images displayed. Axis rotation assessments indicated evidence of qualitative extracellular matrix contraction in the tissue immediately contiguous to the tissue targeted for removal and within the Superficial Zone region when compared to untreated samples.

Figure 4:
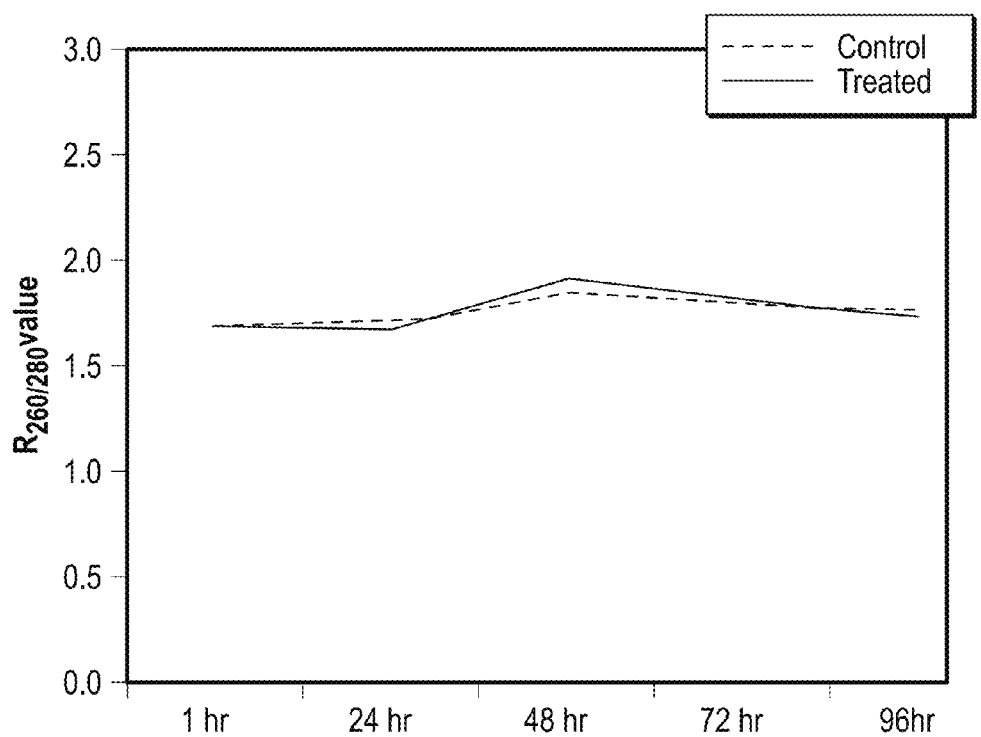
FIG. 4 illustrates $R_{260/280}$ values versus time.

Twenty samples were allocated to this group generating two untreated and treated paired sample explants for each incubation interval for the patient. The RNA quantity obtained included an untreated group concentration of 29.8±9.3 ng/μL and a treated group concentration of 29.7±8.6 ng/μL, with no statistical differences between groups. As depicted in FIG. 4, $R_{260/280}$ values were 1.76±0.06 and 1.76±0.10 for untreated and treated samples, respectively, with no statistical significance between groups at each time period during the incubation. Note the stability of RNA sample purity produced during the testing period for each incubation interval.

Figure 5:
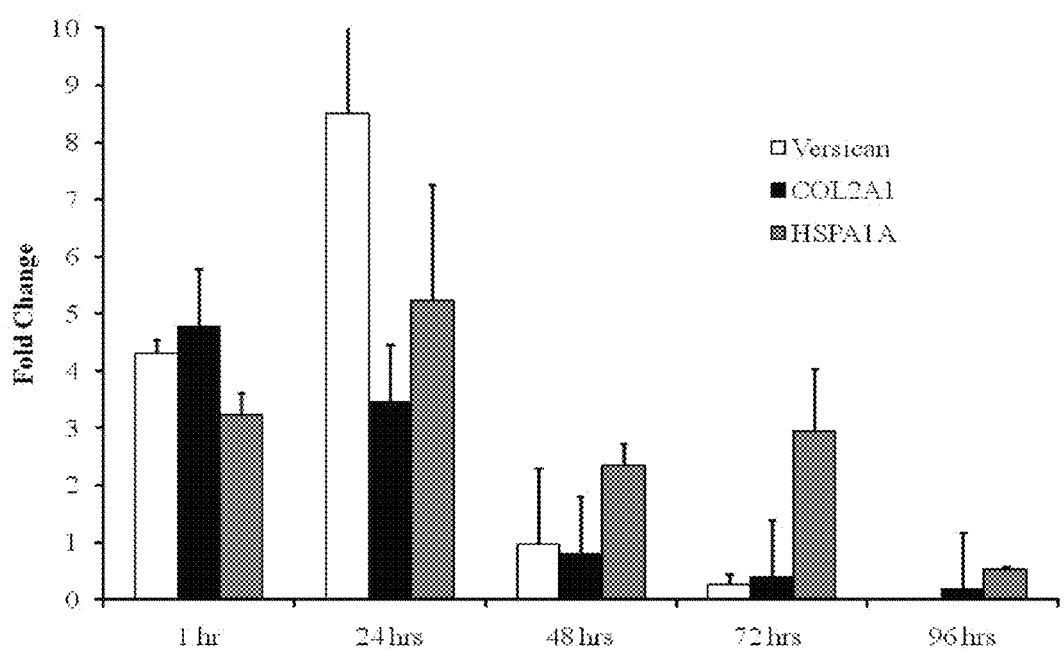
FIG. 5 illustrates RT-PCR results depicting mean fold changes in transcriptional expression of versican, COL2A1, and HSPA1A mRNA in subadjacent surface chondrocyte after non-ablation radiofrequency lesion stabilization.

FIG. 5 depicts the fold change temporal kinetics of mRNA veriscan (CSPG2), COL2A1, and HSPA1A mRNA expression. Data reflects fold change relative to the untreated samples at each incubation interval. The untreated sample group continued to express a stable mRNA level during incubation and did not demonstrate significant fold change variations during the incubation period in any of the mRNAs examined. The treated sample group demonstrated a large fold increase in expression early followed by a reversion to baseline expression comparable to untreated samples. Versican mRNA (CSPG2) was undetectable at 96 hours in the treated samples and its standard deviation at the 24 hour incubation interval was large.

FIG. 6 depicts curve regression fit of the expression events based on concentration kinetic changes modeled as single production versus single removal rates. Note that the high statistical fit reflects a biologic phenomenon of damped exponential activation and deactivation/reaction exhaustion. Inset depicts an enlarged view of the modeled temporal expression kinetics post-treatment. Data reflects treated sample groups compared to the average $\Delta C_T$ of the 1 hour untreated sample group serving as control and as time zero. The curve regression fit was statistically significant with strong relevance for versican ($R^2=0.72$; $p<0.04$), COL2A1 ($R^2=0.92$; $p<0.0004$), and HSPA1A ($R^2=0.83$; $p<0.002$), demonstrating a scaled temporal response similar to the fold change assessment based upon the control of each incubation interval.

Early post-treatment chondrocyte viability is not effected within tissue contiguous to the treatment site during non-ablation radiofrequency lesion stabilization. Subadjacent surface articular cartilage chondrocytes treated as disclosed herein demonstrated one or more of the following: continued viability for 96 hours post-treatment, a lack of increased nuclear fragmentation or condensation, persistent nucleic acid production during incubation reflecting cellular assembly behavior, and a transcriptional up-regulation of matrix and chaperone genes indicative of retained biosynthetic differentiated cell function.

These activities support the efficacy of early surgical intervention; namely, to safely eliminate the irritant of damaged tissue without iatrogenic injury to contiguous tissue, to stabilize the remaining healthy tissue through chondrosupportive matrix modifications, and to induce an appropriate in situ biosynthetic cellular response within the tissue subadjacent to the lesion that retains differentiated function. While removing the irritant of damaged tissue may slow lesion progression and permit local homeostatic and repair responses to occur less encumbered, the results of this study suggest that it is possible to manipulate or induce cellular function thereby recruiting local chondrocytes to aid lesion recovery. Early surgical intervention can be viewed as a tissue rescue. Articular cartilage will continue to display biologic responses appropriate to its function, rather than converting to a tissue ultimately governed by the degenerative material property responses of matrix failure. If so, early intervention would impact the late changes and disease burden of damaged articular cartilage.

Versican mRNA expression was evaluated in this study because it is translated into a chondroitin sulfate proteoglycan that resides as aggregates within the inter-territorial matrix at articular surfaces. This site specificity reflects its functional role in the Superficial Zone extracellular matrix structure and therefore influences matrix-failure based lesion stabilization of early cartilage damage. The versican proteoglycan displays low chondroitin sulfate density and sulfation levels, a property reflected in the fixed charge density inherent in surface cartilage amenable to modification by physiochemical loading during non-ablation treatment. Since surface damaged articular cartilage displays an altered fixed charge density due to layered proteoglycan depletion, this exposed and accessible charge density is an important therapeutic target during the surface events of lesion stabilization. Further, the normal charge barrier associated with the amorphous layer above the lamina splendens is functionally abolished in damaged articular cartilage surfaces.

Boundary lubrication regimes at normal articular cartilage surfaces provide a unique charge density barrier due to surface active phospholipids which is remarkably resistant to the physiochemical loading deployed during lesion stabilization particularly at sites bathed in sodium chloride as during arthroscopy. This charge density serves as a physiochemical loading barrier to and an intrinsic margin during the surface events of lesion stabilization at intact surfaces. It is a barrier which is robust enough to require enzymatic digestion, trauma, or other means like ablation energy to transgress in order to reach a collagen layer. The transient Versican mRNA transcriptional up-regulation noted in response to lesion stabilization is consistent with prior studies demonstrating post-treatment Superficial Zone phenotype characteristics and may be important in the reconstitution of cartilage surface properties by chondrocytes after removal of the damaged tissue irritant.

More intriguing, however, is that various isoforms of versican have been implicated in actions related to chondrogenesis through mesenchymal condensation, cell aggregation, chondroprogenitor cell promotion, and chondrocyte gene expression. The adult isoform core protein size does not seem to change with osteoarthritis. There is evidence for Superficial Zone progenitor cell populations and chondrocyte proliferation and clustering in early and fibrillated cartilage damage. Versican's mRNA post-translational role during early tissue responses to lesion stabilization may relate to a protective, and possibly transitional, matrix construct during tissue assembly repair events by modulating chondrocyte adhesion, morphology, proliferation, differentiation, or migration similar to its function noted during repair and self-assembly events in other tissue types.

The COL2A1 gene encodes the α-1 chain of type II collagen, the major collagen constituent of articular cartilage matrix and a good marker of an activated functional phenotype. The transcriptional enhancement of COL2A1 after targeted lesion stabilization demonstrated in this study serves as an assessment of the generalized chondrocyte function to promote articular cartilage-specific matrix synthesis. Chondrocytes at the site of lesion stabilization retain the ability to produce mRNA reflective of their differentiated phenotype and characteristic of mature cartilage. This indicates that the responses are not limited to a fibroblastic-like dedifferentiation and low matrix gene expression reflective of the phenotypic alterations of diseased tissue or other cartilage interventions during which chondrocytes continue to express synthetic activity post-treatment.

HSPA1A codes for highly conserved non-steric molecular chaperones that participate in protein stabilization and assembly by mediating folding and transport of existing or newly translated proteins. Chaperones levels are modulated to reflect the status of protein folding requirements within the cell such as preventing newly synthesized proteins and assembled subunits from aggregation into non-functional structures that can occur due to natural macromolecular crowding. Chaperone levels reflect cellular requirements related to biosynthetic responses as a means to monitor changes in cell environment. In chondrocytes, HSPA1A proteins induce chondro-protection against apoptosis and help resist the extracellular matrix destruction of osteoarthritis. HSPA1A is constitutively expressed in chondrocytes while its inducible expression has been related to the terminal differentiation of chondrocytes and is increased in osteoarthritis as an early marker. Although it is presently uncertain if the translational products of versican and COL2A1 are routine protein clients of HSPA1A chaperones within human articular chondrocytes, HSPA1A expression in this study is consistent with the temporal expression kinetics similar to other studies that have linked HSPA1A up-regulation with active matrix production and the reconstruction of chondrons.

It is possible that removal of damaged tissue itself can enable biosynthetic activity in vivo as an unburdened homeostatic or repair response. By removing a biologic and mechanical irritant, the lesion site can be altered to a more favorable perturbation-specific mechanotransductive environment supportive of differentiated gene expression. However, since the tissue in this study was incubated in an unloaded state not reflective of physiologic perturbation specificity, it remains unclear whether the removal of the damaged tissue itself is a signaling mechanism responsible for the increased biosynthetic activity observed. Although the untreated group reflected responses of surface fibrillated articular cartilage incubated in an unloaded environment without significant alteration in baseline mRNA expression studied, the treated samples reflected differentiated biosynthetic function consistent with normal physiologic responses. The signaling mechanisms for these responses are unlikely directly related to the physiochemical loading of the cartilage surfaces utilized during lesion stabilization.

For instance, because the physiochemical loading deployed in this study did not include heat delivery, HSPA1A induction should not be related to a temperature stress as up-regulation in chondrocytes does not occur until temperatures exceed 39° C.; a temperature that, interestingly, is consistent with which exposed but normal extracellular matrix type II collagen begins to denature and that can be deployed in a controlled manner by non-ablation technology for more demanding lesions. Further, and although extracellular pH changes can effect chondrocyte metabolism in culture, chondrocytes are not subjected to extracellular alterations in pH during short-term topical loading in sodium chloride environments. Since non-ionizing electromagnetic forces are generated by non-ablation devices to promote therapeutic biologic responses in tissues unencumbered by necrosis-inducing current deposition, these forces should be considered a plausible induction mechanism at least partly responsible for the biosynthetic temporal response kinetics observed in the treated samples.

For example, tissue temperature and pH are effected by non-ionizing electromagnetic field voltage potentials that can generate local changes in biochemical reaction rates and protein conformation through orienting dipole moments above thermal noise, as well as, stimulate cartilage extracellular matrix production through voltage activated $H^+$ channels altering intracellular pH. Such fields influence ion transporters that regulate cell function, proliferation, differentiation, and migration, and when applied to cartilage have been shown to be chondroprotective, to reduce lesion progression, and to increase chondrocyte proliferation, lacuna formation, gene expression, protein synthesis, and extracellular matrix production. Electromagnetic forces demonstrate activity at independent gene initiation promoter domains through signaling pathways that enable short exposures to induce rapid DNA activation; a mechanism linking protein synthesis to electron charge transport acceleration induced by electromagnetic forces.

Early intervention for articular cartilage damage remains an attractive approach to decrease disease burden because it is this setting that retains the elements in situ for normal cartilage homeostasis and repair. Chondrocyte behavior in culture provide important insight into concepts for in situ cartilage treatment. Maintaining chondrocytes in their normal in vivo position preserves their interactions with their extracellular matrix which are important when examining chondrocyte behavior. The cartilage samples described in the examples were incubated in bulk. At a minimum, the results demonstrate that the chondrocytes within tissue contiguous to the site of targeted lesion stabilization remain viable and are able to express genes appropriate to differentiated chondrocyte function suggestive of tissue repair. In addition, these results demonstrate a small window into the coordinated sequence of a healing event cascade that may be harnessed for further lesion repair and recovery.

Although cartilage has been historically described as a tissue type with a low expectant regenerative potential, the portion of this low regenerative potential that is due to the biologic and mechanical irritant of damaged cartilage is currently unknown. Non-ablation technology allows for the opportunity to evaluate the role that the irritant plays in this low expectant regenerative potential. Whereas the hallmarks of non-reversible articular cartilage lesions are more obvious, the characteristics of self-repair and regeneration at reversible lesion sites and those relative to salvageable lesions are not. Despite the heterogeneity of articular cartilage lesions, chondrocyte viability and a differentiated and healing phenotype at the site of safe damaged tissue removal remain inextricably related to the reversibility of early lesions. Removal of this irritant relative to perturbation specificity is necessary to provide a more favorable environment to express mechanotransductive genes for biosynthesis; and, further, for targeted in situ manipulation of those genes. Even more exciting is the potential to allow boundary lubrication regimes that are depleted with damage to reconstitute over a non-irritated site via self-assembly that may ultimately become a regional substrate for cell homing techniques reflective of homeostasis and repair.

The preceding examples can be repeated with similar success by substituting the generically or specifically described reactants and/or operating conditions of this invention for those used in the preceding examples.

Note that in the specification and claims, "about" or "approximately" means within twenty percent (20%) of the numerical amount cited.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for treating targeted tissue comprising:
localizing an alternating current circuit device tip having electrodes in a conductive solution containing electroactive species in which a targeted tissue of a host is found;
deploying current to the alternating current circuit device tip located in close proximity to the targeted tissue wherein the device tip inhibits electrode-to-tissue contact but permits a shielded reaction zone for the conductive solution to react with at least one electrode of the alternating current circuit device tip;
moving an electron between electrodes of the alternating current circuit device tip utilizing an electron donor and acceptor carrier within the conductive solution containing electroactive species;
producing an electromagnetic field quanta near the targeted tissue when the device tip is placed next to the targeted tissue and producing an electron donor and an electron acceptor carrier associated with a charged specie intermediary created in the conductive solution formed above a baseline dissociation rate;
moving the charged specie intermediary created in the conductive solution toward the targeted tissue surface; and
inducing an effect upon the targeted tissue or the conductive solution that is configured to treat the targeted tissue.

2. The method of claim 1 wherein the effect is produced by inducing gene expression with energy that is not injury inducing to the targeted tissue.

3. The method of claim 1 wherein the effect is produced by inducing superficial extracellular matrix volume contraction.

4. The method of claim 1 wherein the effect is precision resection of the targeted tissue.

5. The method of claim 4 wherein the precision resection of the targeted tissue is produced by denaturing an exposed proteoglycan aggregate of a damaged articular cartilage of the targeted tissue using the charged specie intermediary created in the conductive solution having an induced pH below an isoelectric point of targeted tissue.

6. The method of claim 5 wherein the exposed proteoglycan is a chondroitin sulfate proteoglycan that resides as aggregates within an inter-territorial matrix at an articular surface.

7. The method of claim 1 wherein the effect is stirring of the conductive solution.

8. The method of claim 7 wherein the stirring is microfluidic mixing of the conductive solution.

9. The method of claim 1 wherein the charged specie intermediary created in the conductive solution comprise protons.

10. The method of claim 1 wherein the effect is directing the charged species intermediary created in the conductive solution toward the target tissue.

11. The method of claim 1 wherein the effect is a pharmaceutical agent delivery to the target tissue.

12. The method of claim 1 wherein the effect is an extracellular matrix modification.

13. The method of claim 1 wherein the effect is to upregulate a chondrocyte proliferation.

14. The method of claim 1 wherein the effect is a gene transcription initiation.

15. The method of claim 14 wherein the gene is indicative of a differentiated chondrocyte function.

16. The method of claim 15 wherein the chondrocyte is a surface chondrocyte from the target tissue.

17. The method of claim 14 wherein the gene is selected from Versican, COL2A1 and HSPA1A.

18. The method of claim 1 wherein moving the charged specie intermediary created in the conductive solution toward the targeted tissue surface is directionalized with a plenum.

19. The method of claim 18 wherein the plenum has openings through which the charged specie intermediary created in the conductive solution are thrust.

* * * * *